(12) United States Patent
Sutoris et al.

(10) Patent No.: US 6,200,460 B1
(45) Date of Patent: Mar. 13, 2001

(54) SUBSTANCE MIXTURES CONTAINING STABILIZERS AND COMPOUNDS CONTAINING VINYL GROUPS

(75) Inventors: Heinz Friedrich Sutoris; Hermann Uhr, both of Frankenthal; Konrad Mitulla; Jürgen Schröder, both of Ludwigshafen; Roland Merger, Bad Schönborn; Knut Kessel, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/147,394

(22) PCT Filed: Nov. 28, 1997

(86) PCT No.: PCT/EP97/06651

§ 371 Date: Dec. 16, 1998

§ 102(e) Date: Dec. 16, 1998

(87) PCT Pub. No.: WO98/25872

PCT Pub. Date: Jun. 18, 1998

(30) Foreign Application Priority Data

Dec. 10, 1996 (DE) ................................ 196 51 307

(51) Int. Cl.[7] .............................. C07C 7/20; C07B 63/04
(52) U.S. Cl. .............................. 208/48 AA; 585/4; 585/5; 585/832; 585/950
(58) Field of Search ............................ 208/48 AA; 585/4, 585/5, 832, 950

(56) References Cited

U.S. PATENT DOCUMENTS

| | | |
|---|---|---|
| 3,733,326 | 5/1973 | Murayama et al. . |
| 3,760,005 | 9/1973 | Exner et al. . |
| 4,311,573 * | 1/1982 | Mayhan et al. ................. 204/159.15 |
| 4,383,930 * | 5/1983 | Argabright et al. ............. 252/8.55 D |
| 4,614,827 * | 9/1986 | Arndt et al. ....................... 556/131 |
| 4,665,185 | 5/1987 | Winter et al. . |
| 5,376,151 | 12/1994 | Freeman et al. . |

FOREIGN PATENT DOCUMENTS

| | | |
|---|---|---|
| 18 05 301 | 6/1969 | (DE) . |
| 30 43 164 | 8/1981 | (DE) . |
| 44 16 438 A1 | 11/1995 | (DE) . |
| 195 45 600 A1 | 5/1996 | (DE) . |
| 195 10 184 A1 | 9/1996 | (DE) . |
| 196 09 312 A1 | 9/1997 | (DE) . |
| 196 22 498 A1 | 12/1997 | (DE) . |
| 0 581 737 | 2/1994 | (EP) . |
| 1-165534 | 6/1989 | (JP) . |
| 1 027 150 | 7/1983 | (RU) . |
| 1 139 722 | 2/1985 | (RU) . |
| 1 558 888 A1 | 4/1990 | (RU) . |
| WO 96/16921 | 6/1996 | (WO) . |
| WO 96/17002 | 6/1996 | (WO) . |

OTHER PUBLICATIONS

Inorganic Chemistry (p. 424–425), Meloni, et al. Phthalocyaninato (2–) Chromium (III) Phosphinates.
Chemical Reviews, 1992, Bernard Meunier " Metalloporphyrins as Versatile Catalysts for Oxidation Reactions and Oxidative DNA Cleavage", (p.1411–1456).
Journal of the Chemical Society, 1981, Bowaher, et al. " Use of Alkali– and Alkaline –Earth–Metal Lons in the Template Syntesis of 12–Crown–4, 15–Crown, and 18–Crown–6" (p.1157–1161).
Macrocyclic Polyether Syntheses, 1982, G.W. Gokel, et al.(p. 169–172, 201–208 and 227).
Phase Transfer Catalysts, Merck– Schuchardt (p. 77–80).
Angewandte Chemie, 1986, Donald J. Cram, Praorganisation–von Solventien zu Spharanden (p.1041–1060).
Monographs in Supramolecular Chemistry, "Crown Ethers and Cryptands", George W. Gokel (p. 146–147).
Angewandte Chemie, 1972, C.J. Pederson, et al. :Makrocyclische Polyather und ihre Komplexe (p. 16–26).
Ullmann 's Encyclopedia of Industrial Chemistry, vol. A 10 (p. 284–285).
Ullmann 's Encyclopedia of Industrial Chemistry, vol. A 1 (p. 290–293).

* cited by examiner

*Primary Examiner*—Bekir L. Yildirim
(74) *Attorney, Agent, or Firm*—Oblon, Spivak, McClelland, Maier & Neustadt, P.C.

(57) ABSTRACT

Substance mixtures comprising
(A) vinyl-containing compounds,
(B) an active amount of a mixture inhibiting the premature polymerization of the vinyl-containing compounds, comprising
(i) at least one N-oxyl compound of a secondary amine which carries no hydrogen atoms on the α-C atoms, and
(ii) at least one iron compound,
(C) if appropriate nitro compounds, and
(D) if appropriate costabilizers,
a process for inhibiting the premature polymerization of vinyl-containing compounds (A) and
the use of mixture (B), if appropriate as a mixture with nitro compounds (C) and/or costabilizers (D), for inhibiting the premature polymerization of free radical polymerizable compounds and for stabilizing organic materials against the damaging action of free radicals.

14 Claims, No Drawings

SUBSTANCE MIXTURES CONTAINING STABILIZERS AND COMPOUNDS CONTAINING VINYL GROUPS

The present invention relates to substance mixtures which comprise vinyl-containing compounds, at least one nitroxyl compound and iron compound, if appropriate also nitro compounds, and if appropriate also other costabilizers, a process for the purification or distillation of compounds of this type without premature polymerization thereof taking place, and the use of mixtures which comprise nitroxyl compounds and iron compounds, and if appropriate nitro compounds and/or costabilizers, for inhibiting the premature polymerization of vinyl-containing compounds and for stabilizing organic materials against the damaging action of free radicals.

It is known that many unsaturated compounds on increasing the temperature are prone to polymerization proceeding, as a rule, under free radical conditions. For example, vinylaromatic compounds, such as styrene or α-methylstyrene, must thus be stabilized by suitable compounds in order to prevent premature polymerization during purification by distillation of the crude products obtained on a large scale. Customarily, in this process these stabilizers or polymerization inhibitors are added to the crude products to be distilled before or during the purification step. Despite this measure, considerable amounts of polymers are still obtained. In isolated cases, specially also during operational breakdowns, complete polymerization of the monomers or monomer mixture present can take place during the purification or distillation. High costs result in this case due to the enormous purification outlay and the production loss.

In the Soviet Patent Specifications 1 027 150, 1 558 888 and 1 139 722 the stabilization of styrene by the use of nitroxyl or bisnitroxyl compounds is described.

4-Acylaminopiperidine N-oxyl derivatives are employed in the earlier German Patent Application, 19 510 184.7 for the stabilization of free radical-polymerizable monomers.

The earlier German Patent Application DE 19 609 312.0 describes compositions which comprise vinyl-containing monomers and at least one N-oxyl compound of a secondary amine, the latter possessing no hydrogen atoms on the N-bonded C atoms.

Mixtures of vinylaromatic compounds with sterically hindered nitroxyl compounds which are activated by traces of oxygen are mentioned in the Specification WO 96/16921.

The Japanese Specification Hei 1-165 534 discloses 1-piperidyloxy derivatives as polymerization inhibitors for styrene. U.S. Pat. No. 3,733,326 describes the inhibition of the polymerization of vinyl monomers by the use of free radical precursor compounds.

Mixtures of nitroxyl and nitro compounds for the stabilization of vinylaromatic compounds or vinyl-containing monomers during purification or distillation are described in U.S. Pat. No. 5,254,760 and the earlier German Patent Application 19 622 498.5.

The effectiveness of the stabilizers described in these specifications and the stability of the monomer mixtures containing additives are good, an improved retardation/action being achieved by the higher content of nitro compounds described in the earlier German Patent Application 19 622 498.5. Therefore, in the case of an interruption in the supply of monomers and stabilization additive to the column, a better delaying action as regards time is achieved by these stabilizers up to the commencement of large-scale polymerization reactions.

However, since in these large-scale processes even relatively small amounts of polymers add up to large amounts of undesired by-product, there is a permanent need for even more effective polymerization inhibitors. A reduction in the amount of nitro compounds is also desirable with a view to improved handling by the operating personnel, and a reduction in possible environmental pollution.

It is thus an object of the present invention to make available mixtures of vinyl-containing compounds which are stabilized even more effectively against premature polymerization during purification or distillation.

We have found that this object can be achieved by substance mixtures which contain
(A) vinyl-containing compounds,
(B) an active amount of a mixture inhibiting the premature polymerization of the vinyl-containing compounds, comprising
    (i) at least one N-oxyl compound of a secondary amine which carries no hydrogen atoms on the α-C atoms, and
    (ii) at least one iron compound,
(C) if appropriate nitro compounds, and
(D) if appropriate costabilizers.

Substance mixtures are preferred which contain from 99.9999 to 95% by weight of the component (i) and from 1 ppm to 5% by weight of the component (ii), in each case based on the total mixture (B).

Substance mixtures are particularly preferred which contain from 99.999 to 97% by weight of the component (i) and from 10 ppm to 3% by weight of the component (ii), in each case based on the total mixture (B).

Preferred vinyl-containing compounds (A) are those of the formula (Ia)

where:
$R^1$, $R^2$, $R^3$ and $R^4$ independently of one another are each hydrogen, $C_1$–$C_6$-alkyl, $C_2$–$C_6$-alkenyl, unsubstituted or substituted aromatic or heteroaromatic radicals or halogen,
with the condition that not more than two of these radicals at the same time are unsubstituted or substituted aromatic or heteroaromatic radicals, or $R^1$ and $R^2$ or $R^3$ and $R^4$ together form a saturated or unsaturated $C_3$-, $C_4$-, $C_5$- or $C_6$-alkylene bridge, in which up to two nonadjacent C atoms can be replaced by N, NH, N($C_1$–$C_4$-alkyl), N($C_6$–$C_{10}$-aryl) or oxygen.

The $C_1$–$C_6$-alkyl radicals in this case include the linear alkyl chains from methyl through ethyl up to hexyl but also the corresponding branched radicals. Possible $C_2$–$C_6$-alkenyl radicals are likewise ethenyl, propenyl etc. up to hexenyl and the groups branched in the saturated moiety. Aromatic or heteroaromatic and unsubstituted and substituted groups which may be mentioned, for example, are phenyl, pyridyl, alkylphenyl or -pyridyl, such as methylphenyl or -pyridyl or ethylphenyl or -pyridyl, alkenylphenyl or -pyridyl, such as vinylphenyl or vinylpyridyl, carboxyphenyl or -pyridyl, formylphenyl or -pyridyl, sulfophenyl or -pyridyl, hydroxyphenyl or -pyridyl, aminophenyl or -pyridyl, nitrophenyl or -pyridyl, but also naphthyl or naphthyl substituted by alkyl, alkenyl, carboxyl, formyl, sulfo, hydroxyl, amino or nitro groups. The halogen radical customarily used is fluorine or chlorine, occasionally also bromine.

If, for example, compounds each having an aromatic or heteroaromatic radical on the one hand and a $C_1$–$C_6$-alkyl on the other hand are taken into consideration, then, if the remaining two radicals from $R_1$, $R^2$, $R^3$ and $R^4$ are hydrogen, α-methylstyrene (2-phenyl-1-propene), the two β-methylstyrene isomers (cis- and trans-1-phenyl-1-propene), α-ethylstyrene (2-phenyl-1-butene), the two β-ethylstyrene isomers (cis- and trans-1-phenyl-1-butene) up to α-hexylstyrene (2-phenyl-1-octene) or the two β-hexylstyrene isomers (cis- and trans-1-phenyl-1-octene) result as an example of monomers to be added.

Similarly, when using the pyridyl radical instead of the phenyl radical the compounds 2-pyridyl-1-propene, cis- and trans-1-pyridyl-1-propene, 2-pyridyl-1-butene, cis- and trans-1-pyridyl-1-butene up to 2-phenyl-1-octene and the two isomers cis-1-pyridyl-1-octene and trans-1-pyridyl-1-octene result. Also included here, of course, are the isomers which differ by the position of the pyridine N atoms relative to the bond linking the vinyl group to the pyridyl group. If the phenyl or pyridyl radical is substituted by the above-mentioned groups, compounds such as α-methylstyrenesulfonic acid (2-sulfophenyl-1-propene), α-methylnitrostyrene (2-nitrophenyl-1-propene), α-ethylstyrenesulfonic acid (2-sulfophenyl-1-butene), α-ethylnitrostyrene (2-nitrophenyl-1-butene), the similar pyridyl compounds or the cis/trans-isomers of the corresponding β-substituted compounds result. Of course, also included here are the isomers which result due to the position of the substituent on the benzene ring relative to the phenyl-vinyl bond or, in the case of the substituted pyridine radical, due to the relative position of pyridine N atom, substituent and pyridyl-vinyl bond to one another.

By choice of an aromatic or heteroaromatic radical on the one hand and a $C_2$–$C_6$-alkenyl group on the other hand, it is possible if the two remaining radicals in turn are hydrogen also to derive, inter alia, substituted butadienes as compounds (A). The compounds 1- or 2-phenylbutadiene, 1- or 2-pyridylbutadiene, for example, can be employed with the corresponding cis/trans-isomers on the one hand and, in the case of the pyridyl radical, in turn the positional isomers due to the relative position of the N atom to the pyridyl-vinyl bond. Here also, very different substituents already mentioned above can occur on the aromatic or heteroaromatic system.

Furthermore, according to the invention also aromatic or heteroaromatically substituted ethylenes, such as styrene, vinylpyridine, divinylbenzene, nitrostyrene, styrenesulfonic acid, vinyltoluene and, if appropriate, their isomers can be employed.

According to formula (Ia), in these monosubstituted ethylenes three of the radicals $R^1$, $R^2$, $R^3$ and $R^4$ are hydrogen and only one is an aromatic or heteroaromatic, unsubstituted or substituted group, ie. in the corresponding sequence phenyl, pyridyl, vinylphenyl, nitrophenyl, sulfophenyl and methylphenyl. If desired, disubstituted ethylenes in which two or four radicals $R^1$, $R^2$, $R^3$, $R^4$ are hydrogen and the other radicals are aromatic or heteroaromatic groups can also be employed. Customarily, these are symmetrically substituted stilbenes, such as 4,4'-diaminostilbene, 4,4'-dinitrostilbene, 4,4'-dinitrostilbene-2,2'-disulfonic acid, 4,4'-diaminostilbene-2,2'-disulfonic acid or their cis- or transisomers. Of course, it is also possible to employ those isomers which are different from one another with respect to the position of the substituent or of the substituents in the aromatic or heteroaromatic system relative to the vinyl group. According to formula (Ia), in these stilbenes two of the radicals $R^1$, $R^2$, $R^3$ and $R^4$ are hydrogen and the remaining radicals, which are not arranged vicinally, which in this case are also identical, are in the corresponding sequence aminophenyl, nitrophenyl, nitrosulfophenyl and aminosulfophenyl.

Halogen-containing compounds, such as vinyl chloride, vinylidene chloride, vinyl fluoride, vinyl bromide and chloroprene (2-chloro-1,3-butadiene) can likewise be employed in the claimed mixtures.

If $R^1$ and $R^2$ or $R^3$ and $R^4$ together form a saturated or unsaturated $C_3$-, $C_4$-, $C_5$- or $C_6$-alkylene bridge, then, for example, $R^3$, $R^4$-substituted (or naturally completely equivalently thereto $R^1$, $R^2$-substituted) ring systems such as

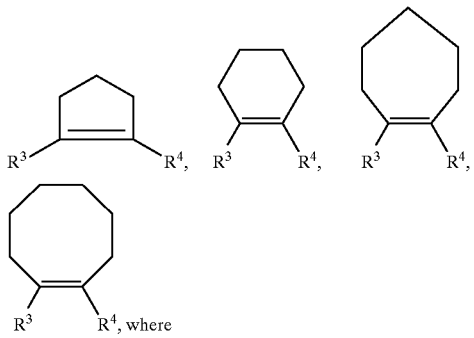

$R^3$ and $R^4$ independently of one another are preferably hydrogen or $C_1$–$C_6$-alkyl and methyl or ethyl are employed as particularly preferred alkyl radicals. These ring systems can furthermore be additionally unsaturated in the alkylene bridge. In this case, ring systems such as, for example

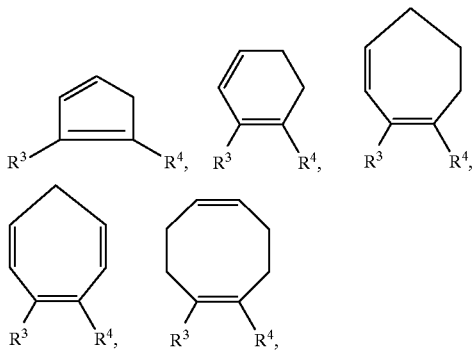

result, where the isomeric compounds should, of course, also be included which differ from one another with respect to the position of the double bonds to one another.

Furthermore, it is possible in these ring systems to replace up to two nonadjacent C atoms by N, NH, N($C_1$–$C_4$-alkyl), N($C_6$–$C_{10}$-aryl) or oxygen.

The following ring systems result as examples, where the compounds isomeric thereto should of course also be included here which result due to the relative position of the heteroatom/heteroatoms to the double bond/double bonds:

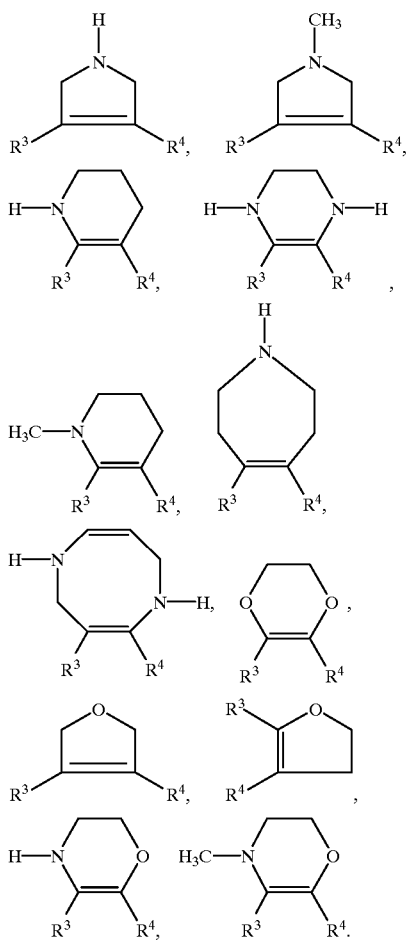

Preferred radicals in the N(C$_1$–C$_4$-alkyl) groups are methyl and ethyl, and in the N(C$_6$–C$_{10}$-aryl) groups phenyl, p-tolyl and mesityl.

Of course, it is possible not only to employ the vinyl-containing compounds in mixtures with their isomers, but also in mixtures with one another, such as are obtained, for example, in the crude products during their preparation.

Furthermore preferred vinyl-containing compounds (A) are those of the formula (Ib)

where

Q is a chemical single bond, oxygen or a group —NZ$^2$—, Z$^1$ is

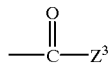

or —Z$^3$,

Z$^2$ is hydrogen, C$_1$–C$_4$-alkyl or together with Z$^3$ is a saturated or unsaturated C$_3$-, C$_4$- or C$_5$-alkylene bridge, in which up to two nonadjacent C atoms can be replaced by N, NH, N(C$_1$–C$_4$-alkyl), N(C$_6$–C$_{10}$-aryl) or oxygen, Z$^3$ is hydrogen, hydroxyl, cyano, C$_1$–C$_8$-alkoxy, C$_1$–C$_8$-alkyl or a radical which together with Z$^2$ forms a saturated or unsaturated C$_3$-, C$_4$- or C$_5$-alkylene bridge, in which up to two non-adjacent C atoms can be replaced by N, NH, N(C$_1$–C$_4$-alkyl), N(C$_6$–C$_{10}$-aryl) or oxygen and up to two CH groups can be replaced by N, and Z$^4$ is hydrogen, C$_1$–C$_4$-alkyl.

If Q is a chemical single bond in formula Ib, the group Z$^1$ is either a radical —CO—Z$^3$ or the group Z$^3$ on its own. Possible radicals Z$^3$ in this case are firstly particularly hydroxyl and C$_1$–C$_8$-alkoxy such as, for example, methoxy, ethoxy, propoxy, t-butoxy or n-butoxy, but also 2-ethylhexoxy, in the latter case cyano.

Z$^4$ is hydrogen or C$_1$–C$_4$-alkyl groups, hydrogen and methyl being preferred radicals. Acrylic acid, methacrylic acid, the corresponding methyl, ethyl, propyl, t-butyl, n-butyl and 2-ethylhexyl esters, and acrylonitrile and methacrylonitrile therefore result as preferred compounds (A) of the formula Ib in the compositions according to the invention.

The compounds (A) of the formula Ib which are contained in the mixtures according to the invention can furthermore contain oxygen as the variable Q. Among these compounds, the vinyl esters are preferred in which the group Z$^1$ corresponds to the radical —CO—Z$^3$, and also the vinyl ethers in which the group Z$^1$ is identical to the group Z$^3$ and in which Z$^3$ is preferably a C$_1$–C$_8$-alkyl group, such as, for example methyl, ethyl, n-propyl, isopropyl, n-butyl, isobutyl, sec-butyl, tert-butyl or 2-ethylhexyl.

If the variable Q is a group —NZ$^2$—, Z$^1$ is preferably a group —CO—Z$^3$.

Beside those already mentioned, suitable radicals Z$^3$ are also those which together with the group —NZ$^2$— form a saturated or unsaturated 5- to 7-membered ring. Examples of such ring systems are:

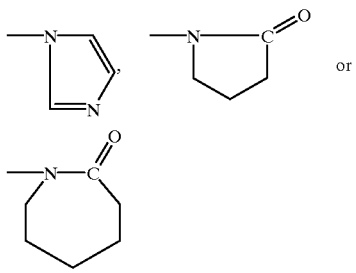

among them particularly the N-pyrrolidinonyl radical and the N-caprolactamyl radical.

The C$_6$–C$_{10}$-aryls mentioned in the radicals N(C$_6$–C$_{10}$-aryl) of the groups Z$^2$ and Z$^3$ preferably include phenyl groups which can be substituted by one or more C$_1$–C$_4$-alkyls. In the case of the presence of two or more substituents, the sum of their C atoms should not be more than four. Exemplary substitution patterns on the benzene ring are, for example, three methyl groups, one methyl and one propyl group or alternatively only one t-butyl group. Further examples of C$_1$–C$_4$-alkyl radicals which can also be present in the radicals N(C$_1$–C$_4$-alkyl) of the groups Z$^2$ and Z$^3$ have already been mentioned above. Possible C$_{10}$-aryl is furthermore also a naphthyl radical.

Preferred compounds (A) in the substance mixtures according to the invention are N-vinylformamide, N-vinyl-2-pyrrolidone, N-vinyl-ε-caprolactam, acrylic acid, vinyl acetate, acrylonitrile, methyl acrylate, n-butyl acrylate and the abovementioned C$_1$–C$_8$-alkyl vinyl ethers.

As component (i) of the mixture (B), the substance mixtures according to the invention contain at least one N-oxyl compound of a secondary amine which does not carry hydrogen atoms on the α-C atoms. These compounds can be present as free compounds or in the form of their salts.

Suitable N-oxyls of amines are, for example, the following structures

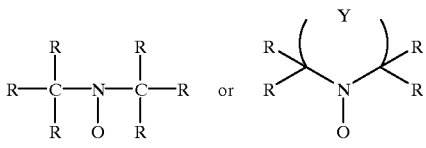

Where R is identical or different alkyl, cycloalkyl, aralkyl or aryl radicals, which can also be bonded in pairs to give a ring system, and Y is a group which is necessary in order to complete a 5- or 6-membered ring. For example, R is a $C_1$–$C_{20}$-, in particular a $C_1$–$C_8$-alkyl radical, a $C_5$- or $C_6$-cycloalkyl radical, a benzyl radical or a phenyl radical. Y is, for example, an alkylene group —$(CH_2)_2$— or —$(CH_2)_3$—.

Furthermore, N-oxyl compounds such as the following structures are also suitable

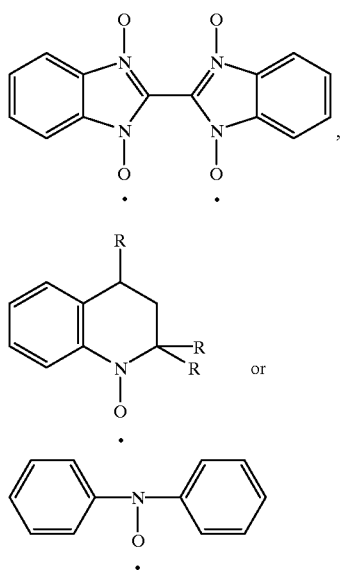

where the aromatic rings can each additionally carry 1 to 3 inert substituents, such as, for example, $C_1$–$C_4$-alkyl, $C_1$–$C_4$-alkoxy or cyano.

Sterically hindered amine derivatives of cyclic amines are preferably employed, eg. of piperidine or pyrrolidine compounds which in the ring can contain a further heteroatom such as nitrogen, oxygen or sulfur, this heteroatom not being in the neighboring position to the hindered amine nitrogen. The steric hindrance is provided by substituents in both neighboring positions to the amine nitrogen, possible substituents being hydrocarbon radicals which replace all 4 hydrogen atoms of the α-$CH_2$ groups. Examples which may be mentioned as substituents are phenyl, $C_3$–$C_6$-cycloalkyl, benzyl and in particular $C_1$–$C_6$-alkyl radicals, where the alkyl radicals bound to the same α-C atom can also be bonded to one another to give a 5-membered or 6-membered ring. The radicals listed below under $R^5$ and $R^6$ are particularly preferred. Preferably, derivatives of 2,2,6,6-tetraalkylpiperidine are employed as N-oxyls of sterically hindered amines.

Preferred N-oxyl compounds in the substance mixtures according to the invention are those of the general formula (II)

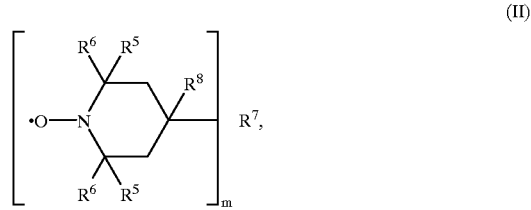

where $R^5$ and $R^6$ independently of one another are each $C_1$–$C_4$-alkyl, phenyl or together with the C atom to which they are bonded are a 5- or 6-membered saturated hydrocarbon ring, $R^7$ is hydrogen, hydroxyl, amino, $SO_3H$, $SO_3M$, $PO_3H_2$, $PO_3HM$, $PO_3M_2$, organosilicon radicals or an m-valent organic or organosilicon radical bonded via oxygen or nitrogen or together with $R^8$ is oxygen or a ring structure defined under $R^8$, M being an alkali metal, $R^8$ is hydrogen, $C_1$–$C_{12}$-alkyl, $C_1$–$C_{12}$-alkoxy or together with $R^7$ is oxygen or together with $R^7$ and the C atom to which they are bonded are the following ring structures

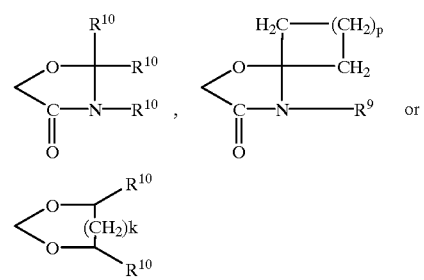

where in the cases in which $R^7$ forms a common radical with $R^8$, m=1, $R^9$ is hydrogen, $C_1$–$C_{12}$-alkyl or —$(CH_2)_z$—$COOR^{10}$, $R^{10}$ is identical or different $C_1$–$C_{18}$-alkyl, k is 0 or 1, z and p independently of one another are each from 1 to 12 and m is from 1 to 100.

$R^5$ and $R^6$ can be $C_1$–$C_4$-alkyl groups, such as methyl, ethyl, n-propyl, isopropyl, n-butyl, isobutyl, sec-butyl or tert-butyl or they can together form a tetra- or pentamethylene group. $R^5$ and $R^6$ are preferably methyl groups.

Suitable $R^8$ radicals are, for example, hydrogen, the abovementioned $C_1$–$C_4$-alkyl groups, and pentyl, sec-pentyl, tert-pentyl, neopentyl, 2,3-dimethylbut-2-yl, hexyl, 2-methylpentyl, heptyl, 2-methylhexyl, 2-ethylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl, (the names isooctyl, isononyl and isodecyl are trivial names and originate from the carbonyl compounds obtained by the oxo synthesis; for this see Ullmann's Encyclopedia of Industrial Chemistry, 5th Edition, Vol. A1, pages 290–293, and Vol. A10, pages 284 and 285) and the alkoxy radicals derived therefrom.

p is preferably 6 to 12, particularly preferably 9.

z is preferably 1 to 4, particularly preferably 2.

Beside hydrogen, suitable $R^9$ is, for example, the $C_1$–$C_{12}$-alkyl groups indicated above. $R^9$ is preferably hydrogen, $C_1$–$C_4$-alkyl or $(CH_2)_z$—$COO(C_1$–$C_6$-alkyl), particularly preferably the radicals —$CH_2$—$CH_2$—$COO(CH_2)_{11}$—$CH_3$ and —$CH_2$—$CH_2$—$COO(CH_2)_{13}$—$CH_3$.

$R^{10}$ can be, for example, one of the abovementioned $C_1$–$C_{12}$-alkyl groups or tridecyl, isotridecyl, tetradecyl, pentadecyl, hexadecyl, heptadecyl or octadecyl. Dodecyl and hexadecyl are preferred.

Preferred monovalent radicals $R^7$ are hydrogen, the $C_1$–$C_4$-alkyl groups already mentioned above and organosilicon radicals of the formula

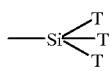

where the groups T can be identical or different and are $C_1$–$C_{12}$-alkyl or phenyl.

Examples of organosilicon radicals of this type are —Si$(CH_3)_3$, —Si$(C_2H_5)_3$,

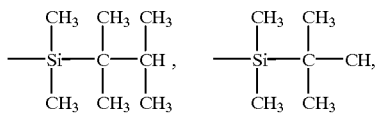

and —Si$(C_6H_5)_3$.

Li, Na and K are preferably employed as alkali metals M in the groups —$SO_3M$, —$PO_3HM$ and —$PO_3M_2$.

Preferred monovalent groups $R^7$ linked via oxygen are hydroxyl and $C_1$–$C_4$-alkoxy groups such as, for example, methoxy, ethoxy, propoxy and t-butoxy, but also the siloxane radicals derived from the above organosilicon radicals.

Preferred m-valent radicals $R^7$ are, for example, the following radicals

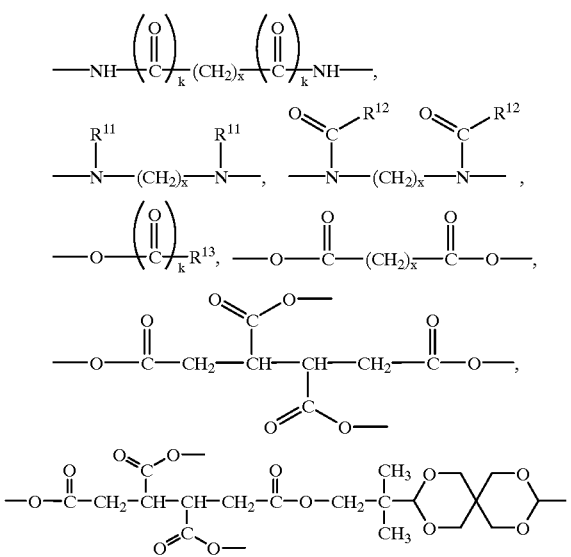

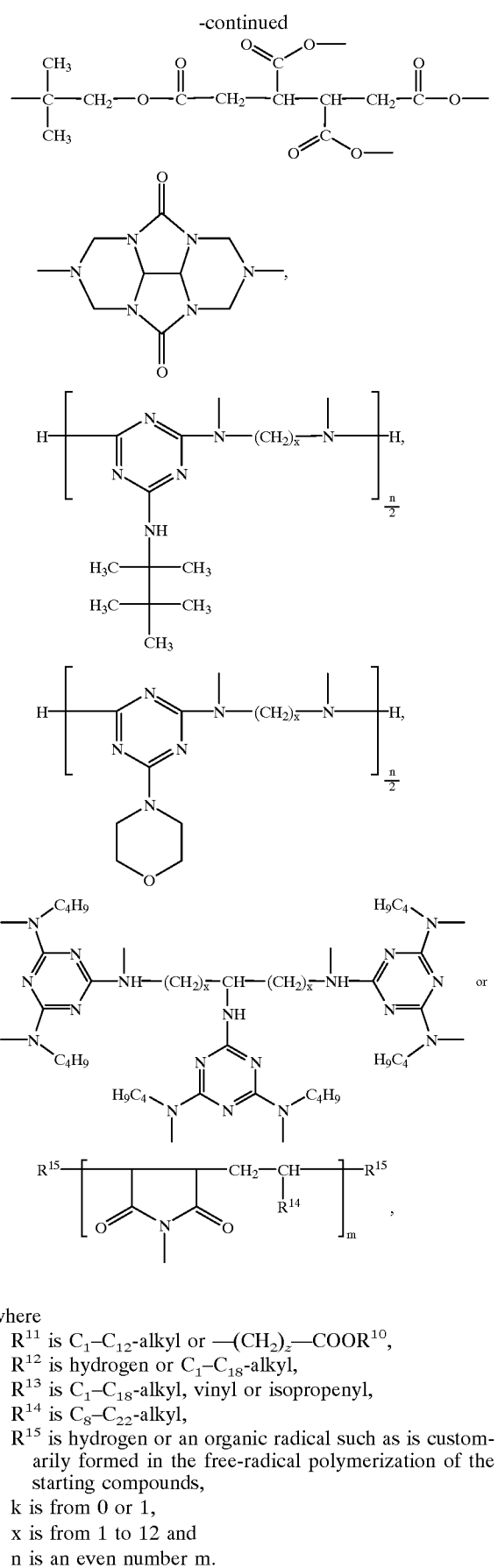

where
$R^{11}$ is $C_1$–$C_{12}$-alkyl or —$(CH_2)_z$—$COOR^{10}$,
$R^{12}$ is hydrogen or $C_1$–$C_{18}$-alkyl,
$R^{13}$ is $C_1$–$C_{18}$-alkyl, vinyl or isopropenyl,
$R^{14}$ is $C_8$–$C_{22}$-alkyl,
$R^{15}$ is hydrogen or an organic radical such as is customarily formed in the free-radical polymerization of the starting compounds,
k is from 0 or 1,
x is from 1 to 12 and
n is an even number m.

If $R^7$ is one of these radicals, $R^8$ is preferably hydrogen. The variable m can in this case be from 1 to 100. Preferably, m is 1, 2, 3, 4 or a number from 10 to 50, as a rule mixtures being employed particularly in the case of the oligomeric or polymeric radicals $R^7$.

Suitable $R^{11}$ radicals are the same as those mentioned for $R^9$. $R^{11}$ is preferably $C_1$–$C_4$-alkyl.

Beside hydrogen, suitable $R^{12}$ radicals are the same as those which have been mentioned for $R^{10}$. $R^{12}$ is preferably hydrogen.

Suitable $R^{13}$ radicals are particularly vinyl, isopropenyl, methyl, ethyl, propyl, i-propyl, t-butyl or $C_{15}$–$C_{17}$-alkyl radicals.

Suitable $R^{14}$ radicals are, for example, the abovementioned $C_8$–$C_{18}$-alkyl radicals and also nonadecyl, eicosyl, uneicosyl and doeicosyl. Mixtures of various radicals $R^{14}$ which differ in the length of the hydrocarbon chain are preferred here.

The radicals $R^{15}$ are hydrogen or organic radicals, such as are formed in the free-radical polymerization of the starting compounds, ie., for example, a radical which is formed from the polymerization initiator or from an intermediately occurring free radical or another radical of this type, such as is familiar to the person skilled in the art.

Radicals $R^{15}$ of this type can be, in the case of the starting compound styrene, for example

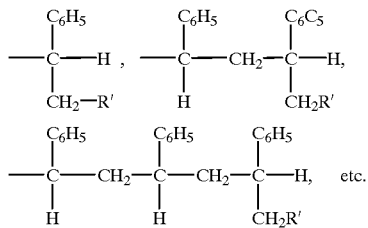

where R' is any desired primary free radical initiating the polymerization of the styrene, or in the general case of the compounds (A).

Furthermore, it is also possible to employ nitroxyl compounds of the formula (II')

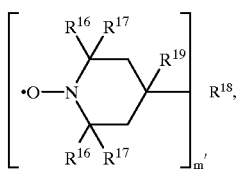

(II')

where
- $R^{16}$ and $R^{17}$ independently of one another are each $C_1$–$C_4$-alkyl, phenyl or, together with the C atom to which they are bonded, are a 5- or 6-membered saturated hydrocarbon ring,
- $R^{18}$ is an m'-valent radical bonded via carbon, oxygen or nitrogen,
- $R^{19}$ is hydrogen, $C_1$–$C_{12}$-alkyl, $C_1$–$C_{12}$-alkoxy, or, together with $R^{18}$, an m'-valent radical bonded via carbon or nitrogen to the C atom carrying these groups by a chemical double bond or, together with $R^{18}$ and the C atom carrying these groups, a saturated isocyclic or heterocyclic 3- to 7-membered ring,
- m' is 1, 2 or 3.

In the case where $R^{18}$ and $R^{19}$ together are an m'-valent radical bonded via carbon or nitrogen by means of a chemical double bond, it is intended to be implied by the values 1, 2 or 3 of the variables m' that, of course, 1, 2 or 3 of the piperidinyl rings shown in formula (II') are each bonded to the m'-valent radical via a double bond.

The choice of the radicals $R^{16}$ and $R^{17}$ agrees with that of the radicals $R^5$ and $R^6$ already mentioned further above and should also be used here. Preferably, methyl groups are again used as substituents $R^{16}$ and $R^{17}$.

Possible m'-valent radicals $R^{18}$ are $C_1$–$C_4$-alkyl, and unsubstituted phenyl and also phenyl substituted by one to three $C_1$–$C_4$-alkyl radicals, examples of $C_1$–$C_4$-alkyl radicals already having been mentioned further above. These radicals can be bonded to the piperidine ring via oxygen, an NH group or alternatively an N($C_1$–$C_4$-alkyl) group. In the case of bonding via a C atom, this should already be appropriately counted as the radical $R^{18}$.

Possible radicals $R^{18}$ are for example (the dashes here mark the free valencies):

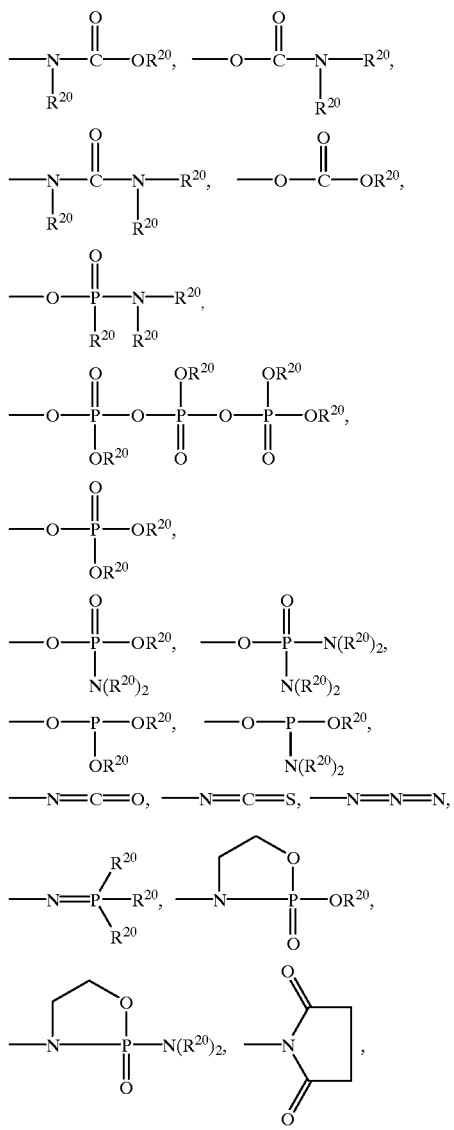

-continued

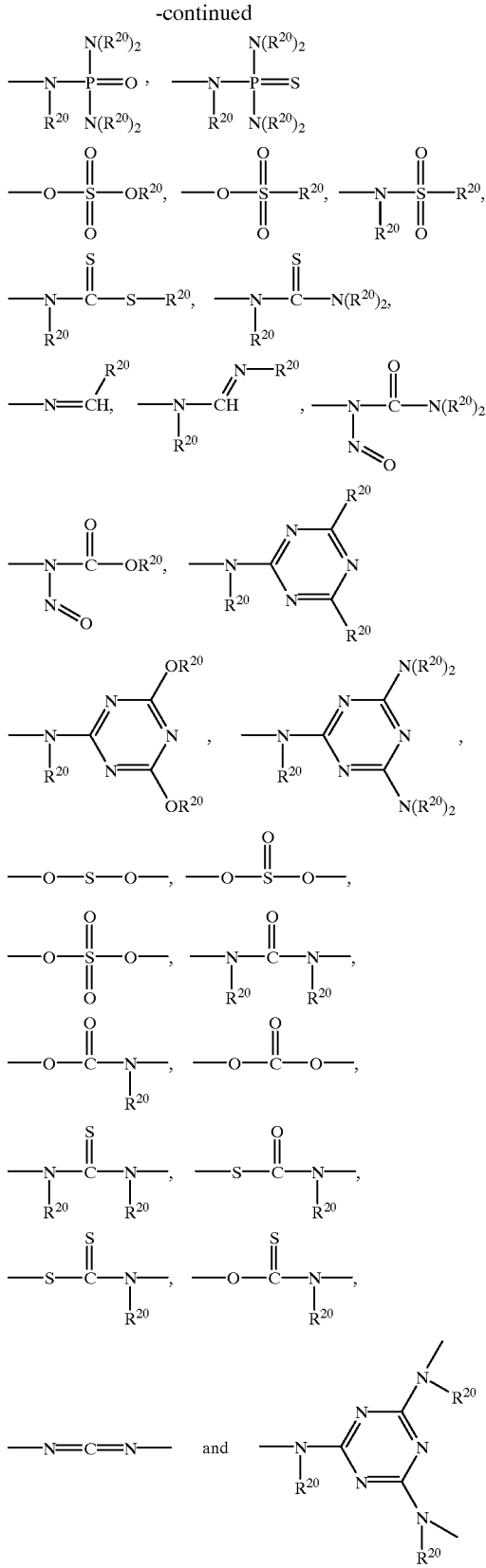

The $C_1$–$C_{12}$-alkyl and $C_1$–$C_{12}$-alkoxy groups which can be considered as possible representatives of the radicals $R^{19}$ have already been discussed as examples for the radicals $R^8$ further above. The radicals $R^{18}$ and $R^{19}$ can also together form a group which is then bonded via carbon or nitrogen to the C atom carrying the groups (the C atom in position 4 of the piperidine ring) by a chemical double bond. m'-valent groups of this type can be for example (the dashes mark the free valencies):

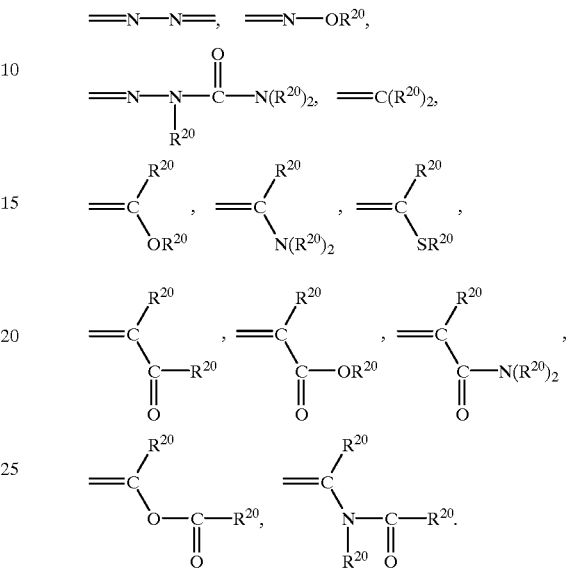

The radicals $R^{18}$ and $R^{19}$ with the C atoms carrying these groups can furthermore form a 3- to 7-membered isocyclic or heterocyclic ring.

Examples of such rings are, for example:

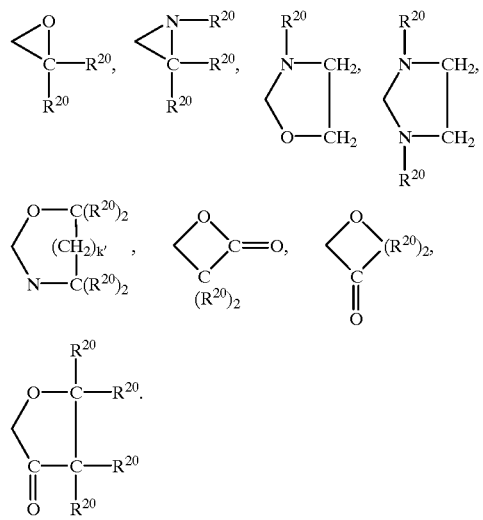

The groups $R^{20}$ are in this case hydrogen, $C_1$–$C_{12}$-alkyl and unsubstituted phenyl or phenyl substituted by one to four $C_1$–$C_4$-alkyl groups. Examples of appropriate $C_1$–$C_{12}$-alkyl groups and $C_1$–$C_4$-alkyl groups which can occur as substituents on the phenyl ring are already mentioned further above. The variable k' can assume a value of 0, 1 or 2.

Further suitable N-oxyls are also oligomeric or polymeric compounds which have a polysiloxane as the main polymer chain and are substituted in the side chain by N-oxyl groups which are derived from 2,2,6,6-tetraalkylpiperidine. The preferred N-oxyl group used here is the 2,2,6,6- tetramethylpiperidine N-oxyl radical. Examples of such N-oxyls likewise to be employed according to the invention are found in the specification WO 69/17002. Examples of syntheses of the amino compounds on which the N-oxyls are based are furthermore mentioned in this specification.

Preferred nitroxyl compounds as component (i) of the substance mixtures according to the invention are also the following:

1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl (4-tert-butyl) benzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexyhydroterephthalate,
N,N'-bis(1-oxyl-2,2,6,6-tetramethylpiperidin-4-yl) adipamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris[N-butyl-N-(1-oxyl-2,2,6,6,-tetramethylpiperidin-4-yl]-s-triazine,
N,N'-bis(1-oxyl-2,2,6,6-tetramethylpiperidin-4-yl)-N,N'-bisformyl-1,6-diaminohexane,
4,4'-ethylenebis(1-oxyl-2,2,6,6-tetramethylpiperazin-3-one) and
tris(2,2,6,6-tetramethyl-1-oxylpiperidin-4-yl) phosphite.

The nitroxyl compounds can be prepared from the corresponding amino or piperidine compounds by oxidation, e.g. with hydrogen peroxide. Details of this oxidation are mentioned, for example, in the earlier German Patent Application 195 101 84.7. The secondary amines which do not carry any hydrogen atoms on the α-C atoms, such as piperidine compounds, and their preparation are generally known. Since the oxidation reactions do not always proceed to completion, the amino or piperidine compounds and partially oxidized intermediates such as, for example, hydroxylamines serving as starting compounds can also be contained in the substance mixtures according to the invention.

In addition, it is of course also possible in the substance mixtures according to the invention for substituted hydroxylamines to be present which have been formed by free radical capture reaction with the vinyl-containing compounds employed or already-formed oligomeric units of the compounds employed. For example, compounds can then be present such as

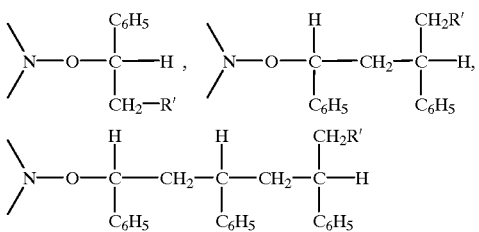

etc., if as compound (Ia), for example, styrene is employed or alternatively

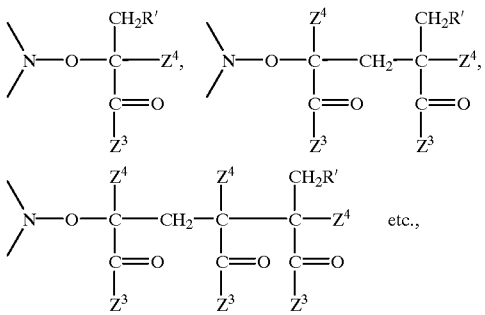

(the two dashes on the N atom are bonds to the radical of the nitroxyl compound to be employed according to the invention)

if as vinyl-containing compound, for example, an acrylic acid derivative of the formula

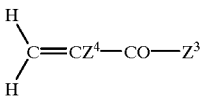

(these compounds form a subset of the compounds of the formula Ib already mentioned above) is employed. The radicals R' here are any desired primary radicals initiating the polymerization of the compounds.

As component (ii), the substance mixtures claimed contain at least one iron compound from the group consisting of the a) iron carbonyls and carbonylferrates,
b) organometallic iron carbonyl compounds,
c) unsubstituted and substituted ferrocene compounds
d) iron compounds with ligands which as donor atoms contain oxygen, nitrogen, sulfur or phosphorus on their own or as a mixture,
e) iron halide and iron pseudohalide compounds.

Group a) includes, for example, compounds such as iron pentacarbonyl, $Fe(CO)_5$, diiron nonacarbonyl, $Fe_2(CO)_9$, triiron dodecacarbonyl, $Fe_3(CO)_{12}$, or hexairon octadecacarbonyl, $Fe_6(CO)_{18}$, which are soluble without exception in less polar or nonpolar media. Further mention can be made here of the carbonyl ferrates such as $M_2Fe(CO)_4$, $M_2Fe_2(CO)_8$ and $M_2Fe_3(CO)_{11}$, where M is an equivalent of an alkali metal or alkaline earth metal. The corresponding Na compounds are preferably employed.

Organometallic iron carbonyl compounds of group b) are, for example, compounds of the formula

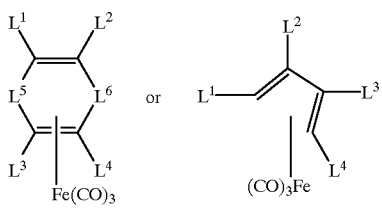

where the variables

L$^1$–L$^4$ are hydrogen, C$_1$–C$_4$-alkyls such as methyl, ethyl, propyl or t-butyl L$^5$, L$^6$ are —(CH$_2$)$_n$— or —CO—, where for the variables L$^5$ and L$^6$ n independently of one another denotes 0,1,2 or 3.

As examples here, the Fe compounds may be mentioned

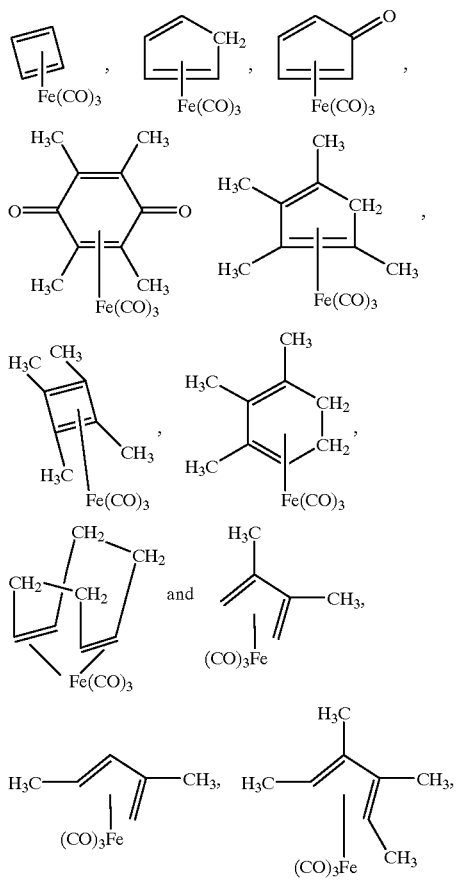

Furthermore, it is also possible to use from this group according to the invention divalent Fe compounds such as [H$_5$C$_5$Fe(CO)$_2$]$_2$, [(H$_3$C)$_5$C$_5$Fe(CO)$_2$]$_2$ and the ferrates M[Fe(CO)$_2$C$_5$H$_5$] and M[Fe(CO)$_2$(H$_3$C)$_5$C$_5$] derived therefrom, here also M being an equivalent of an alkali metal or alkaline earth metal and the corresponding Na compounds preferably being used.

The compounds of group c) to be employed according to the invention include ferrocene itself and the derivatives substituted on one or both cyclopentadienyl rings. It is furthermore also possible to employ dimeric ferrocene derivatives. The individual ferrocene units are linked here via one C atom each of the cyclopentadienyl ring by means of a chemical bond or a methylene, ethylene, propylene, butylene or phenylphosphine bridge.

Possible substituents of the cyclopentadienyl rings are C$_1$–C$_4$-alkenyl radicals, C$_7$–C$_{10}$-aroyl, C$_1$–C$_4$-alkyl radicals such as methyl, ethyl, n-propyl, i-propyl, n-butyl, i-butyl, sec-butyl or t-butyl. It is furthermore possible to replace one or two CH$_2$ or CH$_3$ groups in these substituents by O, NH, NCH$_3$ or OH, NH$_2$. These heteroatoms or heteroatom-containing fragments are bonded here to C atoms. One or two CH$_2$ groups can furthermore also be replaced by CO or one or two CH$_3$ groups by CN. In addition, if desired beside the alreadymentioned groups, it is also possible for diphenylphosphine radicals to function as substituents on the cyclopentadienyl rings.

Examples of ferrocene derivatives to be employed according to the invention are

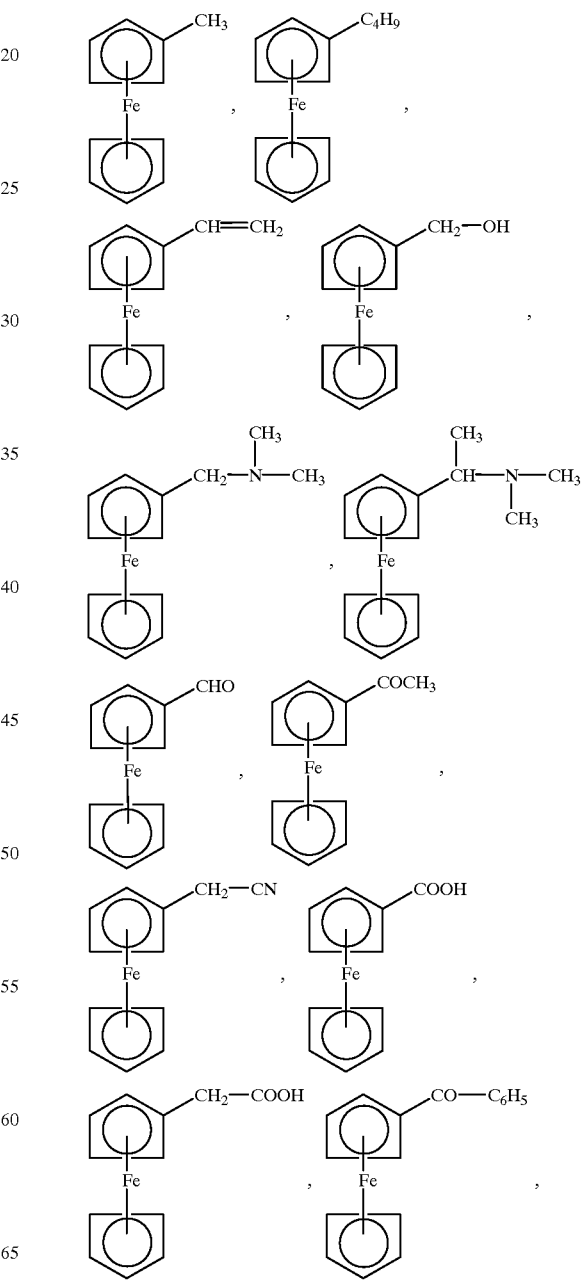

-continued

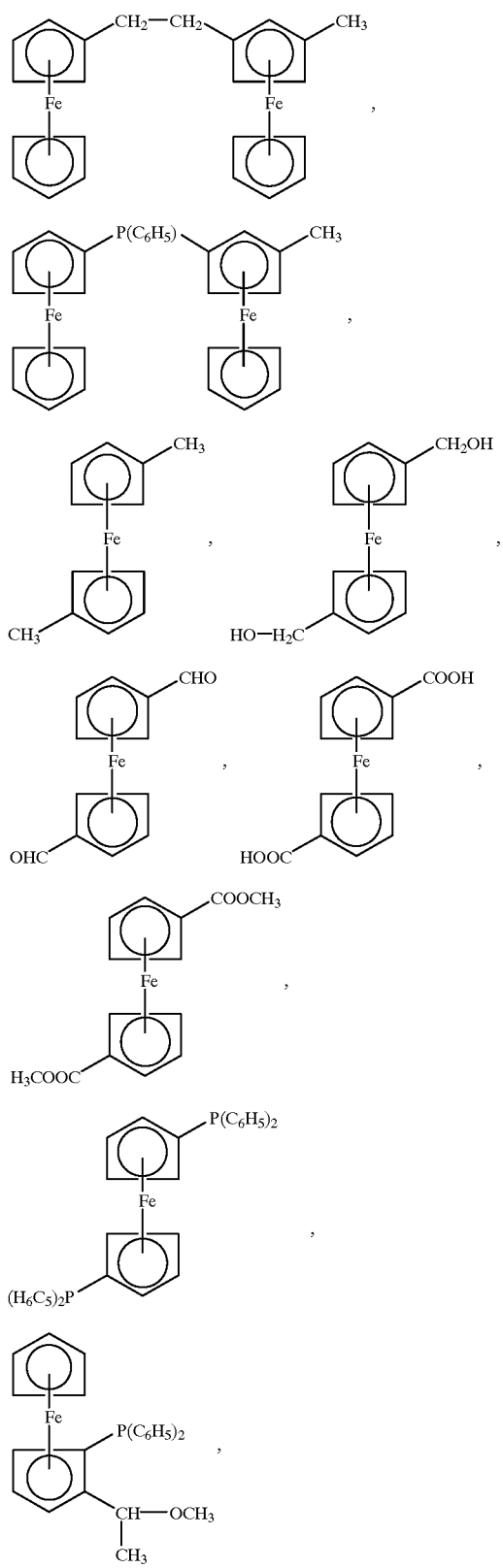

-continued

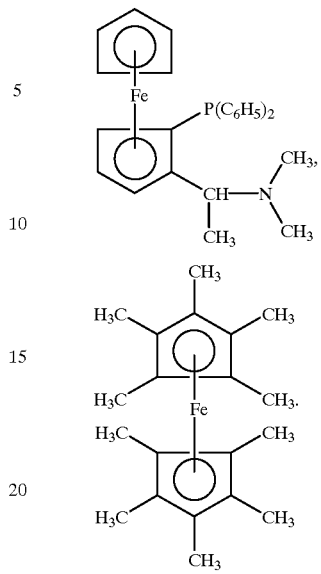

Compounds of group d) which can be employed, for example, are complexes or salts of Fe(II)/Fe(III) with O-containing ligands such as sulfate, acetate, oxalate, citrate, tartrate, lactate, gluconate or acetylacetonate (acac), ie. compounds such as $[Fe_3O(SO_4)_6(OH)_3]^{5\ominus}$, $[Fe_3O(O_2CCH_3)_6(OH_2)_3]^{\oplus}$, $[Fe_3O(O_4C_2)_6(OH_2)_3]^{5\ominus}$, $[Fe(C_4H_4O_6)_2]^{2\oplus/\oplus}$, $Fe(C_4H_4O_6)$, $Fe_2(C_4H_4O_6)_3$, $Fe(C_3H_5O_3)_2$, $Fe(C_6H_{11}O_7)_2$, $[Fe(C_2O_4)_3]^{3\ominus}$, $FeC_2O_4$, $[Fe(C_2O_4)_2]^{2\ominus}$, $Fe(acac)_3$, $Fe(acac)_2$, $Fe(C_6H_6O_7)$, $Fe(C_6H_5O_7)$.

Further exclusively or mainly O-containing ligands for Fe(II) or Fe(III), however, can also be polycyclic ethers such as spherands, cryptands, cryptaspherands, hemispherands, coronands or open-chain representatives of these ethers, and podands. Besides oxygen atoms, many representatives of these compound classes also additionally contain nitrogen and/or sulfur and/or phosphorus and/or arsenic atoms. A description of ligands of this type which, together with Fe(II) or Fe(III), can be used for the preparation of the Fe compounds to be employed according to the invention is found in the literature, e.g. C. J. Pedersen, H. K. Frensdorff, "Makrocyclische Polyether and ihre Komplexe" [Macrocyclic polyethers and their complexes], Angew. Chem. 84 (1), pp. 16–26, 1972; G. Gokel, "Crown ethers & Cryptands", Publ. by Roy. Soc. Chem., Black Bear Press Cambridge, England, 1991; D. J. Cram, "Pr äorganisation—von Solventien zu Sphäranden" [Preorganization—from solvents to spherands], Angew. Chem. 98, pp. 1041–1060, 1986; Phase Transfer Catalysts, Merck-Schuchardt Firmenschrift; G. W. Gokel, S. H. Korzeniowski, "Macrocyclic Polyether Synthesis", Springer Verlag Berlin, Heidelberg, N.Y., pp. 55–151, 1982; U.S. Pat. No. 3,760,005, but where arsenic-containing ligands should not be used. If oxygen and/or the other heteroatoms already mentioned and which may be present are replaced by a cyclic group containing this heteroatom, further compounds are obtained which can be used for the preparation of Fe complexes to be employed according to the invention. Scheme 1 shows an example of a formal conversion of this type:

Scheme 1:

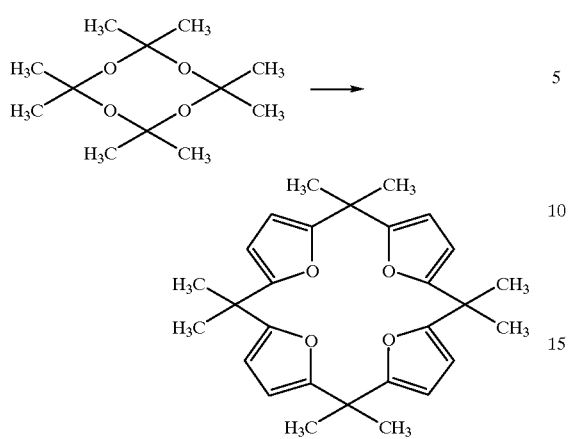

The furan-containing compound can be prepared from acetone and furan in acidic medium with catalysis by alkali metal, alkaline earth metal or transition metal salts (investigations into this have been carried out, for example, by B. R. Bowsher, A. J. Rest, J. Chem. Soc. Dalton, pp. 1157–1161, 1981, and references cited therein), where if Fe salts are used the Fe compounds which are desired and can be employed according to the invention are arrived at directly. Correspondingly, the preparation of "heterocyclophanes" of this type can also be extended to other carbonyl and heterocycle components and thus provide an access to further Fe complexes which can be employed. The person skilled in the art will expect here that in the case of unsaturated heterocycles coordinative bonding to the Fe atom takes place not only via the heteroatom but also mainly via the π-systems.

It is furthermore possible to use complexes with N-containing chelate ligands such as ethylenediamine (en), 1,10-phenanthroline (phen), 1,8-naphthpyridine (napy), 2,2'-bipyridine (pipy) and dibenzo[b,i]-1,4,8,11-tetraaza-(14) annulene (taa), ie. compounds such as [Fe(en)(H$_2$O)$_4$]$^{2\oplus/3\oplus}$, [Fe(en)$_2$(H$_2$O)$_2$]$^{2\oplus/3\oplus}$, [Fe(en)$_3$]$^{2\oplus/3\oplus}$, [Fe(phen)$_3$]$^{2\oplus/3\oplus}$, [Fe(napy)$_4$]$^{2\oplus/3\oplus}$, [Fe(bipy)$_4$]$^{2\oplus/3\oplus}$ and (Fe(taa))

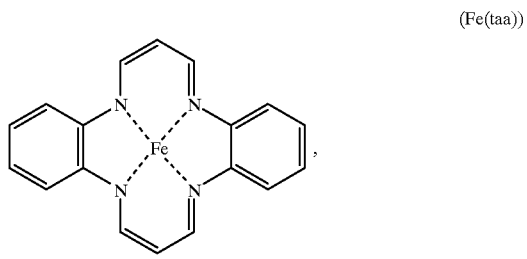

but also complexes of iron with various, substituted porphyrin ligands, such as are known from the literature (for example B. Mennier, Chem. Rev., Vol. 92 (8), pp. 1411–1456, 1992). Other N-containing ligands are phthalocyanine and derivatives thereof. The Fe complexes can easily be prepared starting from Fe compounds, such as Fe(CO)$_5$, and unsubstituted or substituted o-phthalonitrile or benzo-fused dinitriles (for preparation see, for example, E. G. Makoni et al., anorg. Chem. 6, p. 424, 1967):

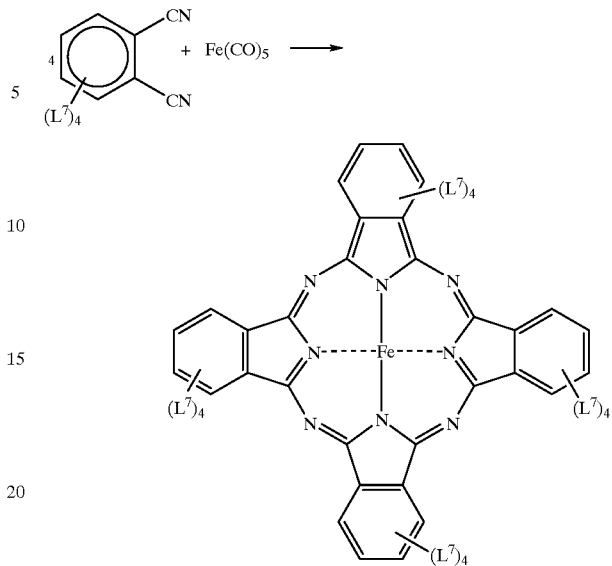

The benzo-fused Fe complexes are obtained similarly:

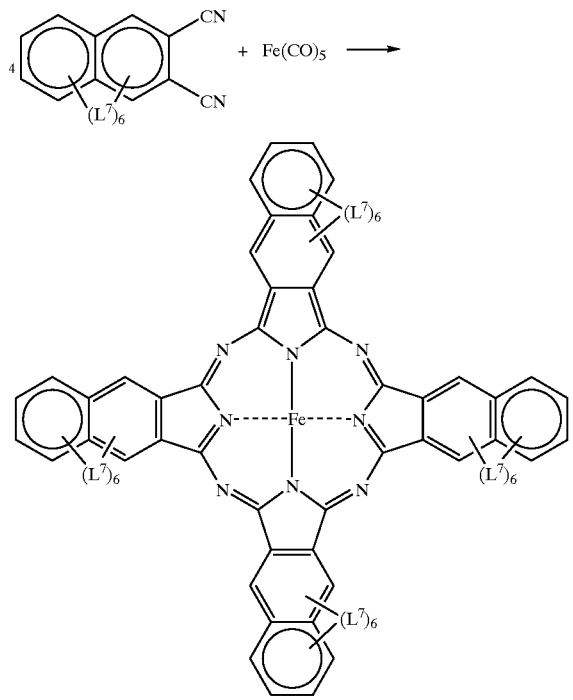

it also being possible, of course, to employ mixtures of various dinitriles as starting material. The radicals L$^7$ independently of one another can be hydrogen, halogen, SO$_3$H, SO$_2$NH$_2$, SO$_2$NH (C$_1$–C$_{12}$-alkyl), SO$_2$N(C$_1$–C$_{12}$-alkyl)$_2$, CONH$_2$, CONH(C$_1$–C$_{12}$-alkyl), CON(C$_1$–C$_{12}$-alkyl)$_2$, cyano, hydroxyl, C$_1$–C$_{12}$-alkyl, C$_1$–C$_{12}$-alkoxy or C$_1$–C$_{12}$-alkylthio. Preferred halogens are Cl and Br. Corresponding examples of C$_1$–C$_{12}$ radicals were already given further above. Further N- and N,O-containing ligands which can be employed for the preparation of Fe compounds which can be used according to the invention can be inferred from the specification DE-A 4 416 438.

Using N,O-containing ligands, such as ethylenediaminetetraacetic acid (EDTA) or nitrilotriacetic acid (NTA), compounds such as

[Fe(EDTA) (H$_2$O)]$^{\ominus/2\ominus}$, [Fe(NTA) (H$_2$O)$_2$] or [Fe(NTA) (H$_2$O)$_2$]$^\ominus$, afford with 8-hydroxyquinoline (chin) or 5-methyl-8-hydroxyquinoline (H$_3$C-chin) compounds such as

[Fe(chin)$_3$]/[Fe(chin)$_3$]$^{2\ominus}$ or [Fe(H$_3$C-chin)$_3$]/[Fe(H$_3$C-chin)$_3$]$^{2\ominus}$, which can be used likewise.

Fe complexes with azo dyes are mentioned in the specifications U.S. Pat. No. 5,376,151 and DE-A 19 546 600.

Iron-containing dyes of this type can also be employed according to the invention.

Further Fe compounds having N,O-containing chelate ligands to be employed according to the invention have the following formulae

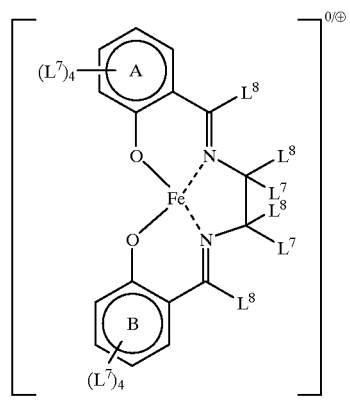

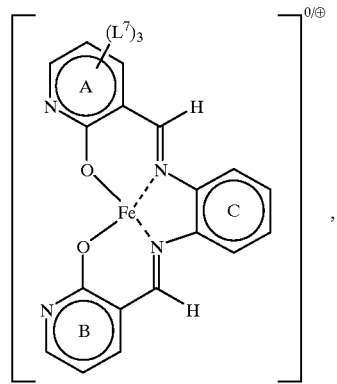

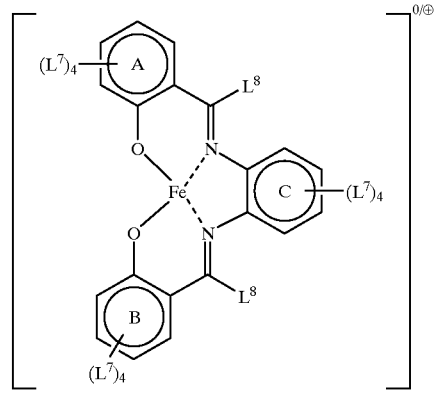

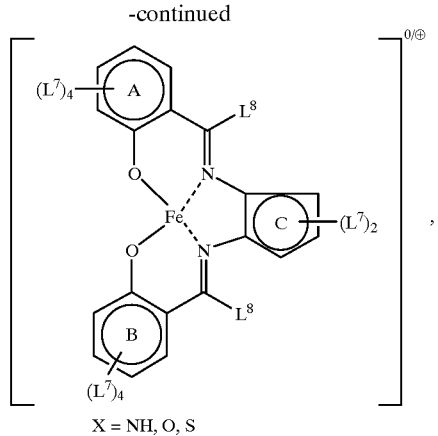

X = NH, O, S

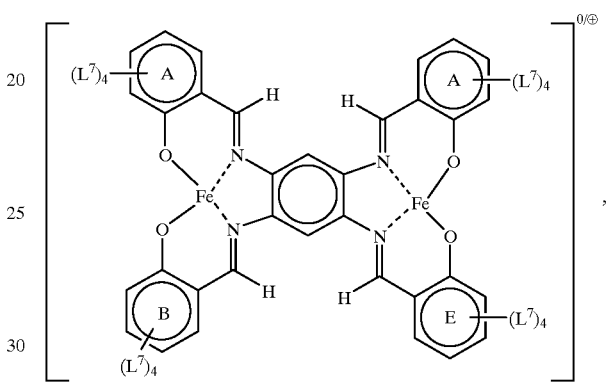

Where the radicals L$^7$ have the meaning already indicated further above. The radicals L$^8$ independently of one another are hydrogen, cyano, C$_1$–C$_{12}$-alkyl, C$_1$–C$_{12}$-alkoxy or halogen, Cl and Br being preferred. The aromatic or heteroaromatic rings A, B, C, D and E can moreover be benzo-fused, the radicals L$^7$ present in each case of the then benzo-fused rings A, B, C being distributed on the remaining six positions. "0/⊕", for example, indicates, depending on whether Fe(II) or Fe(III) is present in the complex, the total charge (ie. 0 in the presence of Fe(II), +1 ("⊕") in the presence of Fe(III)).

Examples of Fe compounds of this type are

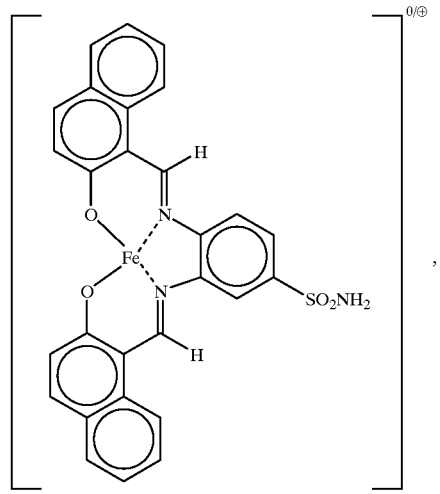

-continued

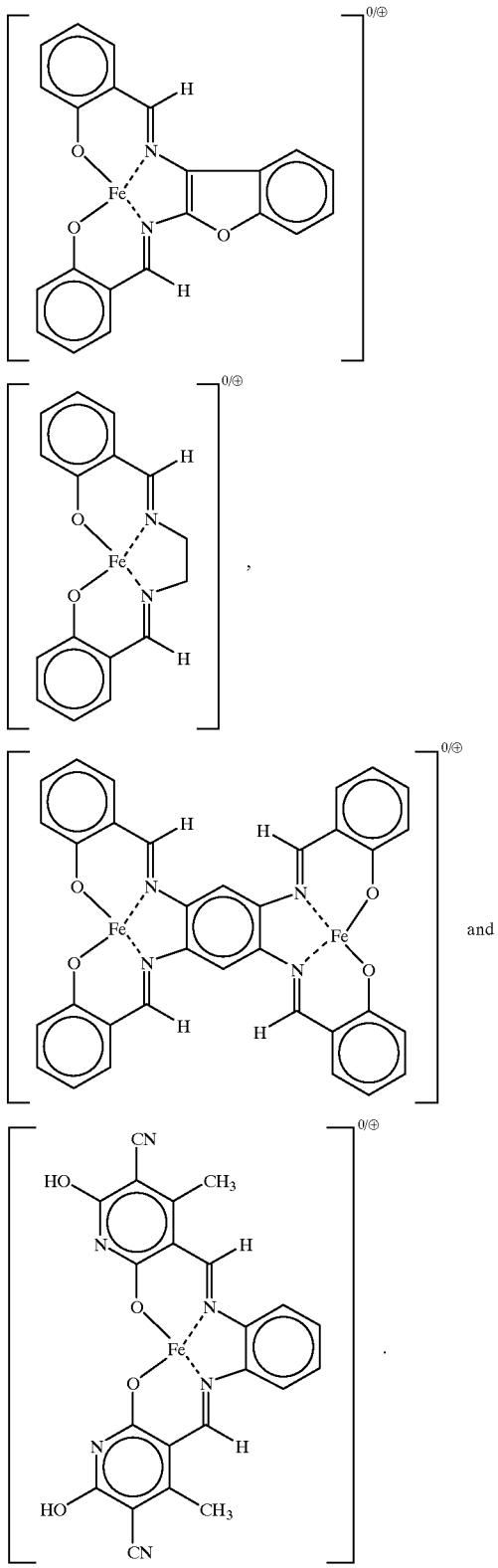

The preparation of these N,O-containing ligands is well known and is generally carried out by condensation of aromatic or heteroaromatic α-hydroxyaldehydes with an aliphatic or aromatic diamine or polyamine. The ligands are then reacted with an Fe salt in aqueous solution.

Other Fe compounds having S-containing ligands which can be used are, for example

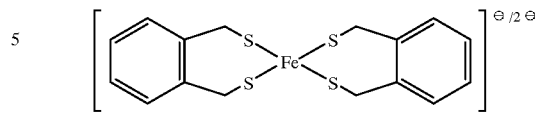

or $[Fe_4S_4(SR)_4]^{4\ominus/3\ominus}$, but also complexes of Fe(II)/Fe(III) with dithiocarbonates $R_2NCS_2^\ominus$ such as, for example [Fe$(S_2CNR_2)_3]^\ominus$ (R=CH$_3$, C$_2$H$_5$).

Furthermore, compounds of group e) can also be employed. In the case of the Fe halides, the Fe(II) and Fe(III) salts of Cl and Br, and also the complex compounds $FeX_4^{\ominus/2\ominus}$ (X=Cl,Br), are preferably employed. The Fe pseudohalide compounds which can be employed according to the invention include, for example, $[Fe(CN)_6]^{3\ominus}/[Fe(CN)_6]^{4\ominus}$ and also thiocyanate complexes of the series $[Fe(SCN)_{3-X}(H_2O)_{3+X}]^{X\oplus}$ (x=0,1,2).

The counterions used for all negatively charged complex ions mentioned are preferably $H^\oplus, Na^\oplus, K^\oplus$ and ammonium ions $NH_4^\oplus$ and also $N(CH_3)_4^\oplus$, in the case of the hexacyanoferrates, however, beside $K^{61}$ also $Fe^{2\oplus}$ in the case of $[Fe(CN)_6]^{3\ominus}$ and $Fe^{3\oplus}$ in the case of $[Fe(CN)_6]^{4\oplus}$.

In the case of the positively charged complex ions mentioned, $Cl^\ominus, Br^\ominus, I^\ominus, SO_4^{2\ominus}, H_3CCO_2^\ominus, CrO_4^{2\ominus}, BF_4^\ominus$ and also $B(C_6H_5)_4^\ominus$ are preferably employed as counterions.

Of course, due to the synthesis but also under the special conditions to which the substance mixtures according to the invention are subject, mixtures of iron compounds can be present in which the Fe centers have different oxidation states.

It may furthermore be noted that due to reaction with the components present in the substance mixtures according to the invention, the iron compounds employed can differ from the actually active compounds. Possible main reaction components for the iron compounds employed here are the vinyl-containing compounds (A), which can be additionally substituted by aromatic or heteroaromatic groups. Precisely groups of this type often form relatively stable ncomplexes with Fe centers (cf. also the organometallic Fe compounds to be employed according to the invention).

For activation of the Fe compounds a pretreatment with peroxo-containing substances can be carried out. Those possible are, for example, $H_2O_2$, Caro's acid and peroxydisulfuric acid and also its mono- or disalts with sodium or potassium, furthermore also organic peracids, such as perbenzoic acid or substituted perbenzoic acid but also peroxo compounds, such as tert-butyl peroxide. Activation is preferably carried out in the presence of the starting material to be employed for the preparation of the desired nitroxyl compound. If desired, it is additionally also possible for nitro compounds (C) and/or costabilisers (D) to be present as well as solvents and/or suspending agents whose chemical identity and amount have to be determined, if necessary, by some preliminary tests or are known to the person skilled in the art.

A further activation of the Fe compounds, particularly if these are only soluble to a small extent in the substance mixtures according to the invention, consists in fine grinding thereof. This grinding, which takes place using the customary aggregates, can be carried out in the dry or moist state, if appropriate on the substance mixture according to the invention. If desired, however, it is also possible to employ or admix customary dispersants. Beside the abovementioned peroxo-containing substances, oxygen, e.g. atmospheric oxygen, can also be used as the only or, alternatively, additional activator. This is effected by grinding in air or under a definitely set mixture of oxygen (air) and an inert gas, such as, for example, nitrogen.

For iron compounds which are poorly soluble in the substance mixtures, a further activation can consist in dissolving or alternatively only beginning to dissolve them in suitable solvents in the presence or absence of the activators mentioned, such as peroxo-containing substances or oxygen, and reprecipitating them again by means of suitable measures. Measures of this type can be, for example, possibly also independently of the solvents used, dilution with a liquid in which the Fe compound is insoluble, neutralization with an acid or alkali, cooling of the solution, freeze-drying or spray-drying.

In the case of the Fe phthalocyanine or of the Fe tetraazaannulene, it is possible, for example, by treatment with oleum to prepare sulfonic acid derivatives which are present in partially dissolved or finely dispersed form and are precipitated by dilution with water. The finely divided suspensions thus obtained can then be activated further using the abovementioned substances, if appropriate after (partial) neutralization, it also being possible again here for the starting compounds to be employed for the preparation of the nitroxyl compounds to be present.

As additional components (C), the claimed substance mixtures can contain at least one aromatic nitro compound of the formula (III)

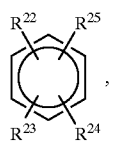
(III)

where
$R^{22}$, $R^{23}$, $R^{24}$ and $R^{25}$ independently of one another are each hydrogen, $C_1$–$C_6$-alkyl, halogen or a radical of the formula CN, SCN, NCO, OH, $NO_2$, COOH, CHO, $SO_2H$ or $SO_3H$,
with the proviso that at least one of the radicals $R^{22}$, $R^{23}$, $R^{24}$ and $R^{25}$ is a nitro group, and the aromatic ring can additionally be benzo-fused.

Possible compounds are, for example,
1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol or 3-iodo-4-cyano-5-nitrophenol. Aromatic nitro compounds are preferably used, such as 2,6-dinitro-4-methylphenol, 2-nitro-4-methylphenol, 2,4-dinitro-6-sec-butylphenol or 2,4-dinitro-6-methylphenol, in which one of the radicals $R^{16}$, $R^{17}$, $R^{18}$ and $R^{19}$ in each case is a nitro, a hydroxyl and a $C_1$–$C_6$-alkyl group.

It is further possible for the substance mixture, if appropriate as a mixture with nitro compound as component (C), additionally also to contain one or more costabilizers (D) from the group consisting of the aromatic nitroso compounds, phenothiazines, quinones, hydroquinones and their ethers, phenols and their ethers, hydroxylamines and phenylenediamines.

Suitable aromatic nitroso compounds are, for example, p-nitrosophenol, p-nitroso-o-cresol or p-nitroso-N,N'-diethylaniline.

Further costabilizers can also be substituted phenols or hydroquinones, for example the following:
4-tert-butylpyrocatechol, methoxyhydroquinone, 2,6-di-tert-butyl-4-methylphenol, n-octadecyl β-(3,5-di-tert-butyl-4-hydroxyphenyl)propionate, 1,1,3-tris-(2-methyl-4-hydroxy-5-tert-butylphenyl)butane, 1,3,5-trimethyl-2,4,6-tris(3,5-di-tert-butyl-4-hydroxybenzyl) benzene, 1,3,5-tris (3,5-di-tert-butyl-4-hydroxybenzyl) isocyanurate, 1,3,5-tris-[β-(3,5-di-tert-butyl-4-hydroxyphenyl)propionyloxy-ethyl]isocyanurate, 1,3, 5-tris-(2,6-dimethyl-3-hydroxy-4-tert-butylbenzyl) isocyanurate or pentaerythrityl tetrakis[β-(3,5-di-tert-butyl-4-hydroxyphenyl)propionate].

For the stabilization of the substance mixtures according to the invention, these contain an effective amount of the mixture (B), if appropriate as a mixture with nitro compounds (C) and/or, if appropriate, costabilizers (D), which in general is from 0.0002 to 5% by weight, preferably from 0.0005 to 0.5% by weight, of the sum of (B) and, if appropriate, (C) and/or (D), in each case based on the total amount of the substance mixture.

Under inert conditions, such as, for example, under a nitrogen atmosphere, it is advantageous to employ mixtures of the mixture (B) according to the invention with at least one nitro compound, suitable substances already being mentioned as examples, as component (C). The suitable ratio of mixture (B) to component (C) is dependent here on the individual boundary conditions such as, for example, the chemical nature of the compounds (A) to be stabilized, the temperature ranges to be adhered to, for example, during a distillation (important, inter alia, in view of the volatility and thus the distribution of the components (B) and (C) between the vapor and liquid phase) or alternatively the (residual) oxygen content in the aggregate used. Taking account of the particular circumstances, it is in each case possible for the person skilled in the art to determine an optimized ratio of these components by means of preliminary tests.

Customarily, a variation in the content of components (B) and (C) in the range from 0.05% by weight to 96.0% by weight or 96.0% by weight to 0.05% by weight, in each case based on the total amount of (B) and (C), is to be assumed.

Since nitroxyl compounds are usually relatively expensive, it is generally attempted to keep their amount small. Component (B) is therefore employed in an amount from 0.05% by weight to 4.5% by weight, and component (C) in an amount from 95.5% by weight to 99.95% by weight based on the total amount of (B) and (C). A content of (B) and (C) from 0.1% by weight to 4.0% by weight or from 99.9% by weight to 96.0% by weight is preferred.

If appropriate, the costabilizers (D) are employed in an amount of the total mixture of the components (B), and, if appropriate, (C) and (D), from 0.01 to 20% by weight.

If the compounds (A) to be stabilized are exposed to an atmosphere which additionally contains amounts of (residual) oxygen, the amount of nitro compounds can be reduced or their use can be dispensed with entirely. This is desirable in view of safety during the handling of inhibitors of this type and from the aspect of reduction of possible damaging effects on the environment. Thus nitroxyl compounds on their own, but to an even greater extent iron-containing mixtures (B) according to the invention have a very good stabilization effect on compound (A) against undesired premature polymerization without addition of nitro compounds at oxygen contents from some 10 to some 10,000 ppm, such as are found, inter alia, in customary large-scale distillation columns.

Of course, the mixtures (B) according to the invention can also contain mixtures of various nitroxyl and iron compounds.

Mixture (B), if appropriate as a mixture with nitro compounds (C) and/or, if appropriate, costabilizers (D), can be added in an effective amount in solid form, as a suspension or as a solution using a suitable solvent before or during purification or distillation in order to suppress premature polymerization. In specific cases, it may also be necessary to add the components (i) and (ii) to the mixture (B), and, if appropriate, nitro compounds (C) and/or one or more of the costabilizers (D) mentioned, separately and in that case preferably at spatially different positions.

It may further be necessary to add part mixtures such as, if appropriate, for example, a mixture of component (i) mixed with nitro compounds (C) and/or, if appropriate, with further costabilizers (D) on the one hand and component (ii) on the other hand separately and in that case preferably at spatially different positions. This procedure is preferably chosen if component (ii) is iron compounds which are readily soluble in the monomer mixtures to be stabilized, but poorly soluble or not soluble at all in the media used during the preparation of the nitroxyl compounds.

Suspensions or solutions of the inhibitor mixtures which, beside mixture (B), if desired can contain nitro compounds (C) and/or costabilizers (D), are preferably prepared using water. Furthermore, alkanols, such as methanol, ethanol, propanol, and n-, i- and t-butanol, if appropriate as a mixture with water, are preferably employed. These alcohols or their mixtures with water are preferably used in the case of the corresponding esters of acrylic acid and alkylacrylic acid.

Furthermore, suspending agents or solvents which can also be used, if appropriate as a mixture with alcohols and water, are ketones such as, for example, acetone, methyl ethyl ketone, methyl propyl ketone, methyl butyl ketone, diols such as glycol or propylene glycol and their alkyl mono- or diethers, oligomeric or polymeric ethylene glycols (polyethylene glycols) and propylene glycols (polypropylene glycols) and their alkyl ethers, diamines such as ethylenediamine or propylenediamine and their alkyl mono- or diimino ethers, oligomeric or polymeric ethylenediamines (polyethyleneimines) and their alkylimino ethers. of course, the compounds (A) employed or their mixtures can also be used as solvents or suspending agents.

Furthermore, crude product mixtures can also be employed for this purpose. If, for example, furnace oil, a mixture obtained in the dehydrogenation of ethylbenzene, which consists mainly of styrene, ethylbenzene, toluene and additionally further substituted aromatics, is to be purified by distillation, this mixture can be employed as a solvent and/or suspending agent.

The stablllizer mixtures (B) according to the invention, if appropriate as a mixture with nitro compounds (C) and/or, if appropriate, costabilizers (D), can be generally used, in solid form or as a suspension or solution, for the inhibition of the premature polymerization of preferably free radical-polymerizable compounds and exhibit their stabilizing action in a wide temperature range. They are effective at any customary storage temperature from −50 to +50° C. and also at elevated temperatures, such as are used, for example, in the distillation or purification of vinyl-containing compounds. The pressure range of the stabilization process is also uncritical. The stabilizers act at normal pressure, but also at reduced or elevated pressure.

Furthermore, the mixture (B) according to the invention, if appropriate with addition of nitro compounds (C) and/or costabilizers (D), can be generally employed for the stabilization of organic materials against the damaging action of free radicals. Organic materials here are understood as meaning, for example, plastics such as polyacrylates, polyolefins, PVC, etc. These are furthermore binders, such as are used, for example, for automotive lacquers or exterior paints (wood preservatives, masonry paints, etc.), or mineral oils and lubricants. The mixtures according to the invention can also be used as a component in appropriate formulations for the protection of biological/organic material such as, for example, the skin in skin protection and sunscreen compositions. Of course, toxicologically questionable additives such as, for example, nitro compounds (C) are not possible here. Moreover, with respect to the components (i), (ii) and, if appropriate, costabilizers (D), a combination suitable for cosmetic applications must be produced, which can be effected by a person skilled in the art familiar with formulations of this type.

EXAMPLES

I. Nitroxyl Compounds Employed
a) N,N'-Bis(1-oxyl-2,2,6,6-tetramethylpiperidin-4-yl)-N,N'-bis-formyl-1,6-diaminohexane

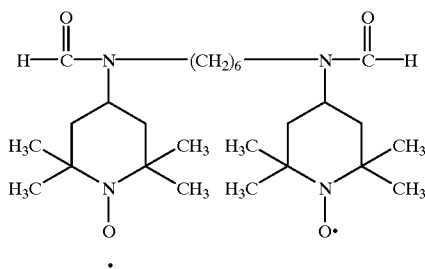

A solution of 337.5 g (0.75 mol) of N,N'-bis-[2,2,6,6-tetra-methylpiperidin-4-yl]-N,N'-bisformyl-1,6-diaminohexane in 600 ml of methanol was treated with 0.15 g of $MgSO_4$. 600 ml of a 30% strength $H_2O_2$ solution (5.87 mol) were added dropwise at 67° C. in the course of 6 h. The temperature was then increased to 81° C. and the mixture was kept at this temperature for a further 6 h, the pH of 7.8 being kept constant by metered addition of a 50% strength KOH solution. The pH was then adjusted to 9.0 by addition of KOH solution. After the mixture had been left at this pH for a further 2 h, the methanol was distilled off, the product being precipitated. It was washed with water and dried.

Characterization shows that the product obtained (called F in the following) contains up to approximately 60 mol % of the dinitroxyl compound of the above formula.

b) Bis(1-oxy)-2,2,6,6-tetramethylpiperidin-4-yl) sebacate

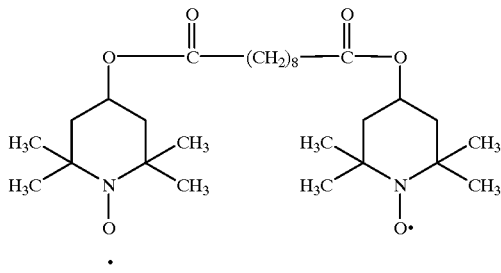

The nitroxyl compound was prepared according to the specification U.S. Pat. No. 4,665,185 ("Example 7", first part of the synthesis of the corresponding hydroxylamine described there) employing the underlying amine compound and using $Mo(CO)_6$ and tertiary-butyl hydroperoxide in methylene chloride as a solvent and obtained in approximately 90% yield by recrystallization from an ethanol/water mixture (in the following this nitroxyl compound is called TEMPO-S).

c) 1-Oxyl-2,2,6,6-tetramethyl-4-hydroxypiperidine

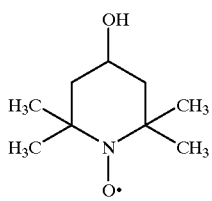

This compound (called H-TEMPO in the following) is a commercially available product (HÜLS).

d) 1-Oxyl-2,2,6,6-tetramethyl-4-(trimethylsilyloxy)piperidine

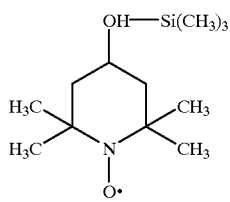

34.2 g (0.2 mol) of H-TEMPO and 64.4 g (0.4 mol) of hexamethyldisilazane were stirred at 126° C. for 4 h. The reaction mixture was concentrated in vacuo. The resulting residue was taken up in methylene chloride, the solution was concentrated in vacuo and the residue was dried in a high vacuum. The yield was 98.9%. The nitroxyl compound is called TMS-TEMPO in the following.

II. Preparation of the Stabilizers

Preparation of Stabilizer 1

A solution of 337.5 g (0.75 mol) of N,N'-bis-[2,2,6,6-tetra-methylpiperidin-4-yl]-N,N'-bisformyl-1,6-diaminohexane and 600 ml of methanol was treated with 0.15 g of MgSO$_4$. 600 ml of a 30% strength H$_2$O$_2$ solution (5.87 mol) were added dropwise at 67° C. in the course of 6 h. The temperature was then increased to 81° C. and the mixture was kept at this temperature for a further 6 h, the pH of 7.8 being kept constant by metered addition of a 50% strength KOH solution. The pH was then adjusted to 9.0 by addition of KOH solution. After the mixture had been left at this pH for a further 2 h, 0.3 g of finely pulverized iron dibenzo-[b, i]-1,4,8,11-tetraaza-(14)annulene dissolved in 50 ml of methanol was slowly added and the methanol was distilled off after 2 h, the product precipitating. It was washed with water and dried (stabilizer 1).

Since the added iron compound is insoluble under the preparation conditions mentioned, it is recovered quantitatively as a mixture with the nitroxyl compound formed. The iron compound has a catalytic effect on the decomposition of excess H$_2$O$_2$ and is activated in situ in the process. Under the assumption that after the reaction about 60 mol % of the dinitroxyl compound and about 40% of the incompletely oxidized starting material are present and that furthermore a nearly quantative isolation of these compounds has taken place, a mixture of 99.92% by weight of the oxidation products and 0.08% by weight of the Fe(taa) oxidized in situ results.

Preparaton of Stabilizer 2

A mixture of 99.2% by weight of TEMPO-S and 0.8% by weight of finely pulverized Fe(taa) was prepared (stabilizer 2).

Preparation of Stabilizer 3 a) 1 g of iron dibenzo[b,i]-1,4,8,11-tetraaza-(14)annulene (Fe(taa)) was suspended in 50 ml of methanol and 10 ml of 30% strength H$_2$O$_2$ was slowly added dropwise under reflux. When the mixture was free from peroxide, 40 ml of water were added. The solid was filtered off with suction and dried at 80° C. and a pressure of 35 mbar.

b) A mixture of 99.2% by weight of TEMPO-S and 0.8% by weight of the Fe(taa) oxidized according to a) was prepared (stabilizer 3).

Preparation of Stabilizers 4 and 5

A mixture of 99.2% by weight of the nitroxyl compound and 0.8% by weight of the iron compound was prepared.

| Stabilizer | Nitroxyl compound | Iron compound |
|---|---|---|
| 4 | H-TEMPO | oxidized Fe(taa) according to 3a) |
| 5 | TMS-TEMPO | oxidized Fe(taa) according to 3a) |

Preparation of Stabilizers 6 and 7

The following mixtures were prepared from F and 2,4-dinitro-6-sec-butylphenol (DNBP):

| Stabilizer | F (% by weight) | DNBP (% by weight) |
|---|---|---|
| 6 | 2 | 98 |
| 7 | 3 | 97 |

TABLE 1

| Substance mixture | Stabilizer | Compound (A) | T (° C.) | Stabilizer content in substance mixture (% by weight) | Polymer content in the stationary state (% by weight) |
|---|---|---|---|---|---|
| A | F (comparison) | Styrene | 114 | 0.012 | 0.14 |
| B | 1 | Styrene | 110 | 0.012 | 0.01 |
| C | 1 | Styrene | 114 | 0.012 | 0.01 |
| D | TEMPO-S (comparison) | Styrene | 114 | 0.012 | 0.30 |
| E | 2 | Styrene | 114 | 0.012 | 0.10 |
| F | 3 | Styrene | 114 | 0.012 | 0.06 |
| G | H-TEMPO (comparison) | Styrene | 114 | 0.012 | 0.10 |
| H | 4 | Styrene | 114 | 0.012 | 0.01 |
| I | TMS-TEMPO (comparison) | Styrene | 114 | 0.012 | 0.28 |
| J | 5 | Styrene | 114 | 0.012 | 0.00 |
| K | 6 (comparison) | Styrene | 110 | 0.15 | 0.02 |
| L | 7 (comparison) | Styrene | 110 | 0.10 | 0.04 |

III. Mixtures

Stationary Measurements on the Substance Mixtures 500 g of the substance mixtures of styrene (compound (A)) and the various stabilizers mentioned in Table 1 were heated under nitrogen and normal pressure to the temperature T mentioned in Table 1 in a reaction vessel. 250 g per hour of an identical substance mixture were continuously metered in to this temperature-controlled substance mixture and the same amount was continuously removed. The equilibrium polymer content in the stationary state was measured in the outlet.

We claim:
1. A substance mixture, comprising:
(A) a vinyl aromatic compound;
(B) an active amount of a mixture which inhibits the premature polymerization of the vinyl aromatic compound, comprising:
   (i) at least one noxyl compound of a secondary amine which carries no hydrogen atoms on the α-C atoms, and
   (ii) at least one iron compound, and optionally
(C) nitro compounds and (D) costabilizers.

2. A substance mixture as claimed in claim 1, comprising from 99.9999 to 95% by weight of the component (i) and from 1 ppm to 5% by weight of the component (ii), in each case based on -the total mixture (B).

3. A substance mixture as claimed in claim 1, comprising from 99.999 to 97% by weight of the component (i) and from 10 ppm to 3% by weight of the component (ii), in each case based on the total mixture (B).

4. A substance mixture as claimed in claim 1, which as component (i) contains at least one compound of the formula (II)

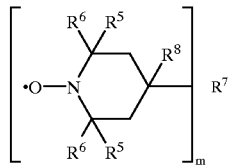

where
R$^5$ and R$^6$ independently of one another are each C$_1$–C$_4$-alkyl, phenyl or together with the C atom to which they are bonded are a 5- or 6-membered saturated hydrocarbon ring,
R$^7$ is hydrogen, hydroxyl, amino, SO$_3$H, SO$_3$M, PO$_3$H$_2$, PO$_3$HM, PO$_3$M$_2$, organosilicon radicals or an m-valent organic or organosilicon radical bonded via oxygen or nitrogen, M being an alkali metal,
R$^8$ is hydrogen, C$_1$–C$_{12}$-alkyl or together with R$^7$ is oxygen or together with R$^7$ and the C atom to which they are bonded are the following ring structures

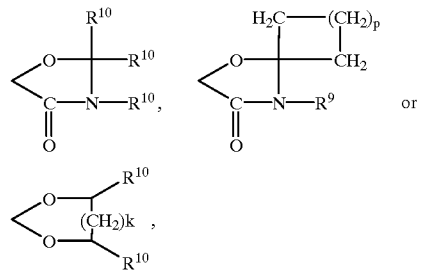

where in the cases in which R$^7$ forms a common radical with R$^8$, m=1,
R$^9$ is hydrogen, C$_1$–C$_{12}$-alkyl or —(CH$_2$)$_z$—COOR$^{10}$,
R$^{10}$ is identical or different C$_1$–C$_{18}$-alkyl,
k is 0 or 1,
z and p independently of one another are each from 1 to 12 and
m is from 1 to 100.

5. A substance mixture as claimed in claim 4, where R$^7$ in formula (II) is a radical of the formula

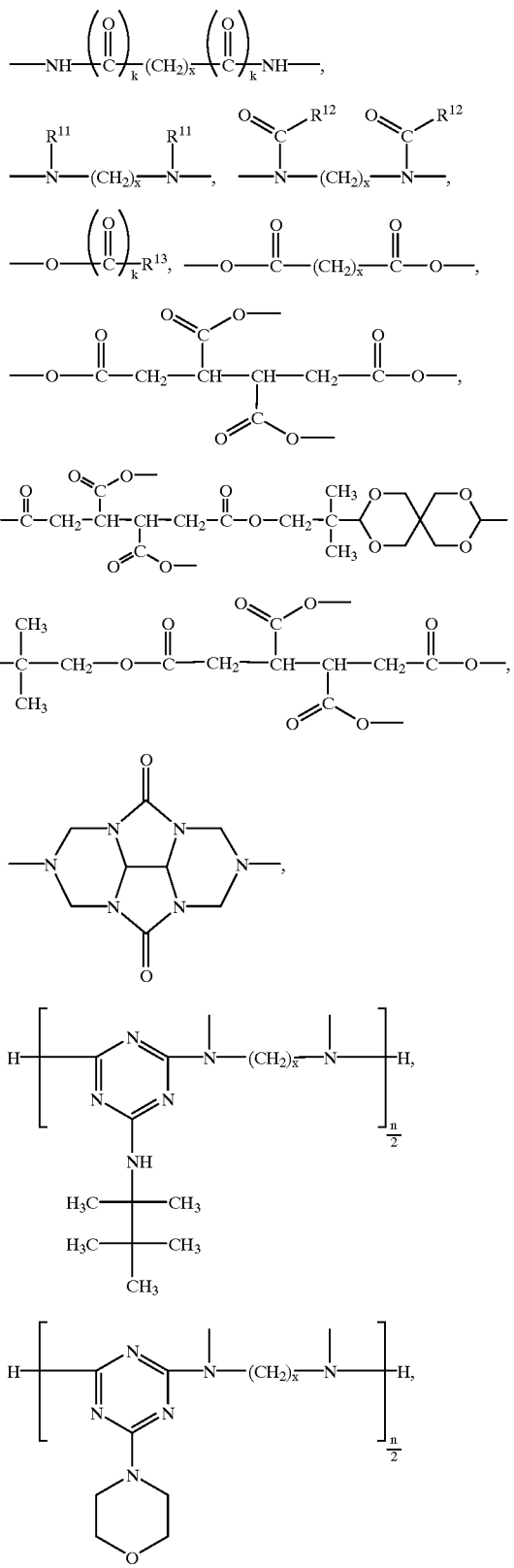

-continued

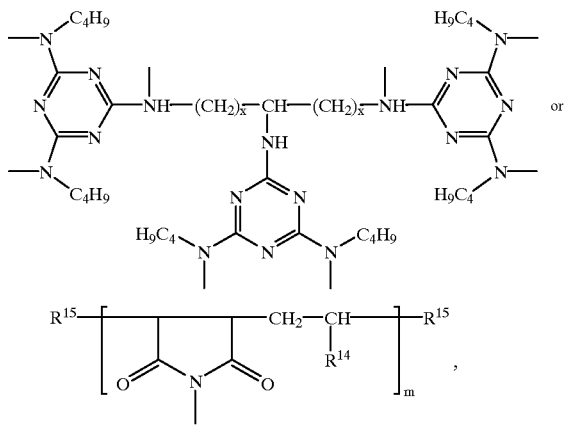

where
- $R^{11}$ is $C_1$–$C_{12}$-alkyl or —$(CH_2)_z$—$COOR^{10}$,
- $R^{12}$ is hydrogen or $C_1$–$C_{18}$-alkyl,
- $R^{13}$ is $C_1$–$C_{18}$-alkyl, vinyl or isopropenyl,
- $R^{14}$ is $C_8$–$C_{22}$-alkyl,
- $R^{15}$ is hydrogen or an organic radical such as is customarily formed in the free radical polymerization of the starting monomers (A),
- k is 0 or 1,
- x is from 1 to 12 and
- n is an even number m.

6. A substance mixture as claimed in claim 1, which as component (ii) contains at least one iron compound from the group consisting of
   a) iron carbonyls and carbonylferrates,
   b) organometallic iron carbonyl compounds,
   c) unsubstituted and substituted ferrocene compounds
   d) iron compounds with ligands which as donor atoms contain oxygen, nitrogen, sulfur or phosphorus on their own or as a mixture,
   e) iron halide and iron pseudohalide compounds.

7. A substance mixture as claimed in claim 1, which as an additional component (C) contains at least one aromatic nitro compound of the formula (III)

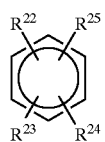

(III)

where
$R^{22}$, $R^{23}$, $R^{24}$ and $R^{25}$ independently of one another are each hydrogen, $C_1$–$C_6$-alkyl, halogen or a radical of the formula CN, SCN, NCO, OH, $NO_2$, COOH, CHO, $SO_2H$ or $SO_3H$, with the proviso that at least one of the radicals $R^{22}$, $R^{23}$, $R^{24}$ and $R^{25}$ is a nitro group, and the aromatic ring can additionally be benzo-fused.

8. A substance mixture as claimed in claim 1, which as an additional component (D) contains one or more costabilizers selected from the group consisting of the aromatic nitroso compounds, phenothiazines, quinones, hydroquinones and their ethers, phenols and their ethers, hydroxylamines and phenylenediamines.

9. A method for inhibiting the premature polymerization of a vinyl aromatic compound (A) as set forth in claim 1 during purification or distillation thereof, which comprises adding to the vinyl aromatic compound (A) in an active amount before or during purification or distillation a mixture (B) and, optionally, nitro compound (C), costabilizer (D) or mixtures thereof.

10. A method for inhibiting the premature polymerization of a vinyl aromatic compound (A) as set forth in claim 1 during purification or distillation thereof, which comprises adding to the vinyl aromatic compound (A) individually in an effective amount in each case before purification or distillation a mixture, the components of the mixture (B) and, optionally, nitro compound (C), costabilizer (D) or mixtures thereof.

11. A method as claimed in claim 10, wherein the components of the mixture (B) and, optionally, nitro compounds (C) and costabilizers (D) are added in spatially different positions.

12. A substance mixture as claimed in claim 1, wherein iron component (ii) is at least one iron compound selected from the group consisting of:
   a) iron carbonyls and carbonylferrates,
   b) organometallic iron carbonyl copompound,
   c) unsubstituted and substituted ferrocene compounds, and
   d) iron compounds with ligands which as donor atoms contain oxygen, nitrogen, sulfur or phosphorus on their own or as a mixture.

13. A method of inhibiting the premature polymerization of free radical-polymerizable compounds, comprising:
   adding stabilizing component (B) and optionally nitro compounds (C) and costabilizers (D) of claim 1 to said free radical-polymerizable compound.

14. A method of stabilizing organic materials against the harmful action of free radicals, comprising:
   adding stabilizing component (B) and optionally nitro compounds (C) and costabilizers (D) of claim 1 to said organic materials.

* * * * *